US007087580B2

(12) United States Patent
Wright et al.

(10) Patent No.: US 7,087,580 B2
(45) Date of Patent: Aug. 8, 2006

(54) NEUROPILIN ANTISENSE OLIGONUCLEOTIDE SEQUENCES AND METHODS OF USING SAME TO MODULATE CELL GROWTH

(75) Inventors: Jim A. Wright, Toronto (CA); Aiping H. Young, Toronto (CA); Yoon S. Lee, Don Mills (CA)

(73) Assignee: GeneSense Technologies, Inc., Toronto (CA)

( * ) Notice: Subject to any disclaimer, the term of this patent is extended or adjusted under 35 U.S.C. 154(b) by 0 days.

(21) Appl. No.: 09/296,264

(22) Filed: Apr. 22, 1999

(65) Prior Publication Data

US 2003/0083274 A1   May 1, 2003

Related U.S. Application Data

(60) Provisional application No. 60/082,791, filed on Apr. 23, 1998.

(51) Int. Cl.
| | |
|---|---|
| A01N 43/04 | (2006.01) |
| C12Q 1/68 | (2006.01) |
| C12N 15/00 | (2006.01) |
| C07H 21/02 | (2006.01) |
| C07H 21/04 | (2006.01) |

(52) U.S. Cl. .......................... 514/44; 435/6; 435/91.1; 435/455; 435/320.1; 536/23.1; 536/24.31; 536/24.5

(58) Field of Classification Search .................... 435/6, 435/91.1, 91.31, 325–366, 375, 320.1, 455, 435/458; 536/23.1–24.3, 24.5, 24.31; 514/44
See application file for complete search history.

(56) References Cited

U.S. PATENT DOCUMENTS 5,801,154 A * 9/1998 Baracchini et al. ............ 514/44
6,391,311 B1 * 5/2002 Ferrara

FOREIGN PATENT DOCUMENTS

| EP | 0128733 | * 12/1984 |
|---|---|---|
| WO | WO94/08625 | 4/1994 |
| WO | WO9507994 | * 3/1995 |
| WO | WO97/15662 | 1/1997 |
| WO | WO97/21808 | 6/1997 |
| WO | WO99/02556 | 1/1999 |
| WO | WO99/04263 | 1/1999 |
| WO | WO99/29729 | 6/1999 |

OTHER PUBLICATIONS

Branch, TIBS 23 pp. 45-50, Feb. 1998.*
Flanagan et al., Nature Biotech. 17: 48-52, Jan. 1999.*
Crystal, Science 270: 404-410, Oct. 1995.*
Ma et al. Biotechnology Annual Review, vol. 5, Jul. 19, 2000, pp. 155-196.*
Jen et al. Stem Cells, vol. 18, 2000, pp. 307-319.*
Green et al. J. Am. Coll. Surg., vol. 191, No. 1, Jul. 2000, pp. 93-105.*
Agrawal et al. Molecular Medicine Today, vol. 6, Feb. 2000, pp. 72-81.*
Bennett et al., Chapter 2 from Methods in Molecular Medicine: Antisense Therapeutics (Ed. Agrawal), Humana. Press Inc. Totowa, N.J., 1996, pp. 13-46.*
Sigmund, Thromb. Vasc. Biol., vol. 20, pp. 1425-1429, 2000.*
Blackshear, Toxicologic Pathology, vol. 29, No. 1, pp. 105-116, 2001.*
He. et al. Ce.., vol. 90: 739-751 (1997).*
Soker et al. J. Biol. Chem. vol. 271(10): 5761-5767 (1996).*
Milner et al. Nature Biotech. vol. 15:537-541 (1997).*
Good and Nielsen; "Inhibition of translation and bacterial growth by polypeptide nucleic acid targeted to ribosomal RNA", PNAS USA (1998) 95:2073-2076.
Sullivan, S.M., "Development of ribozymes for gene therapy", J. Invest. Dermatol. 1(1994) 103(5 Suppl): 85S-89S.
Agrawal, S., "Antisense oligonucleotides: towards clinical trials" Trends Biotechnol., Oct. 1996, 14:376-387.
Crooke S.T., 1998 Antisense Research and Application: Basic Principles of Antisense Therapeutics Ch. 1 pp. 1-50.
Soker S. et al., 1998, Neuropilin-1 is expressed by endothelial and tumor cells as an isoform-specific receptor for vascular endothelial growth factor. Cell 92(92): 735-745.
Curcio, L.D., Bouffard, D.Y., and Scanlon, K.J. Oligonucleotides as modulators of cancer gene expression, Pharmacol Ther. 74:317-32, 1997.
Narayanan, R. and Akhtar, S. Antisense therapy, Curr. Opin Oncol. 8:509-15, 1996.
Ho, P.T. and Parkinson, D.R., Antisense oligonucleotides as therapeutics for malignant diseases, Semin Oncol. 24:187-202, 1997.
Crooke, S.T. and Bennett, C.F. Progress in antisense oligonucleotide therapeutics, Annu Rev. Pharmacol. Toxicol. 36:107-29, 1996.

(Continued)

*Primary Examiner*—Jane Zara
(74) *Attorney, Agent, or Firm*—DLA Piper Rudnick Gray Cary US LLP

(57) ABSTRACT

This invention relates to oligonucleotides complementary to the neuropilin genes which modulate tumor cell growth and angiogenesis in mammals. This invention is also related to methods of using such compounds in inhibiting the growth of tumor cells and angiogenesis in mammals. This invention also relates to pharmaceutical compositions comprising a pharmaceutically acceptable excipient and an effective amount of a compound of this invention.

40 Claims, 15 Drawing Sheets

OTHER PUBLICATIONS

Mitsuhashi, M., "Strategy for designing specific antisense oligonucleotide sequences" J. Gastroenterol. 32:282-7, 1997.

Alama, A. et al., "Antisense oligonucleotides as therapeutic agents", Pharmacol. Res. 36:171-8, 1997.

Brem, S. et al., "Prolonged tumor dormancy by prevention of neovascularization in the vitreous", Cancer Res. 36:2807-12, 1976.

Holmgren, L. et al., "Dormancy of micrometastases: balanced proliferation and apoptosis in the presence of angiogenesis suppression", Nat. Med. 1:149-53, 1995.

Parangi, S. et al., Antiangiogenic therapy of transgenic mice impairs de novo tumor growth, Proc. Acad. Natl. Sci. USA 93:2002-2007, 1996.

Uhlmann et al., Chem. Rev. 90:534-583, 1990.

Agrawal, Antisense Oligonucleotides as Antiviral agents, Trends Biotechnol. 10:152-158, 1992.

Smith et al., Oxygen-Induced Retinopathy in the Mouse, 1994. Invest. Ophthamol. Vis. Sci 35:101-111.

Pierce et al., Vascular endothelial growth factor/vascular permeability factor expression in a mouse model of retinal neovascularization, 1995. Proc. Acad. Natl. Sci. USA 92:905-909.

Tischer, E. et al., "The human gene for vascular endothelial growth factor. Multiple protein forms are encoded through alternative exon splicing", J. Biol. Chem. 266:11947-54, 1991.

Poltorak, Z., et al., "VEGF145, a secreted vascular endothelial growth factor isoform that binds to extracellular matrix", J. Biol. Chem. 272:7151-7158, 1997.

Terman, B.I., et al., "Identification of the KDR tyrosine kinase as a receptor for vascular endothelial cell growth factor", Biochem. Biophys. Res. Commun. 187:1579-86, 1992.

Millauer, B., et al. "High affinity VEGF binding and developmental expression suggest Flk-1 as a major regulator of vasculogenesis and angiogenesis", Cell. 72:835-846, 1993.

Shibuya, M., et al., "Nucleotide sequence and expression of a novel human receptor-type tyrosine kinase gene (flt) closely related to the fms family", Oncogene. 5:519-524, 1990.

De Vries, C., et al., "The fms-like tyrosine kinase, a receptor for vascular endothelial growth factor", Science. 255:989-991, 1992.

Kawakami, A., et al., "Developmentally regulated expression of a cell surface protein, neuropilin, in the mouse nervous system", J. Neurobiol. 29:1-17, 1996.

Takagi, S. et al., "Expression of a cell adhesion molecule, neuropilin, in the developing chick nervous system", Dev. Biol. 170:207-222, 1995.

Soker, S. et al., "Inhibition of vascular endothelial growth factor (VEGF)-induced endothelial cell proliferation by a peptide corresponding to the exon 7-encoded domain of FEGF165", J. Biol. Chem. 272:31582-8, 1997.

He, Z. and Tessier-Lavigne, M. "Neuropilin is a receptor for the axonal chemorepellent Semaphorin III", Cell. 90:739-51, 1997.

Eiglmeier et al., "Use of an ordered cosmid library to deduce the genomic organization of *Mycobacterium leprae*", Molecular Microbiology, 1993, 7(2), pp. 197-206.

Walker et al., "Sequences of 20 Subunits of NADH: Ubiquinone Oxidoreductase from Bovine Heart Mitochondria", J. Mol. Biol., 1992, vol. 226, pp. 1051-1072.

* cited by examiner

Examples of Decreased mRNA Levels following Treatment with Antisense ODNs

Breast Cancer Cells (MDA-MB-231)

Melanoma Cells (A2058)

Effects of GTI3602 Antisense ODN treatment on Human Tumor Growth in Mice

```
ATGGAGAGGG GGCTGCCGCT CCTCTGCGCC GTGCTCGCCC TCGTCCTCGC CCCGGCCGGC    60
GCTTTCGCA ACGATGAATG TGGCGATACT ATAAAAATTG AAAGCCCCGG GTACCTTACA   120
TCTCCTGGTT ATCCTCATTC TTATCACCCA AGTGAAAAAT GCGAATGGCT GATTCAGGCT   180
CCGGACCCAT ACCAGAGAAT TATGATCAAC TTCAACCCTC ACTTCGATTT GGAGGACAGA   240
GACTGCAAGT ATGACTACGT GGAAGTCTTC GATGGAGAAA ATGAAAATGG ACATTTAGG    300
GGAAAGTTCT GTGGAAAGAT AGCCCCTCCT CCTGTGTGT CTTCAGGGCC ATTTCTTTT    360
ATCAAATTTG TCTCTGACTA CGAAACACAT GGTGCAGGAT TTTCCATACG TTATGAAATT   420
TTCAAGAGAG GTCCTGAATG TTCCCAGAAC TACACAACAC CTAGTGGAGT GATAAAGTCC   480
CCCGGATTCC CTGAAAAATA TCCCAACAGC CTTGAATGCA CTTATATTGT CTTTGCGCCA   540
AAGATGTCAG AGATTATCCT GGAATTTGAA AGCTTTGACC TGGAGCCTGA CTCAAATCCT   600
CCAGGGGGA TGTTCTGTCG CTAGACCGG AAAACACCAG GGGATGGATT CCCTGATGTT   660
GGCCCTCACA TGGGCGTTA CTGTGGACAG AAAACACCAG GTCGAATCCG ATCCTCATCG   720
GGCATTCTCT CCATGGTTTT TTACACCGAC AGCGGCGATAG CAAAGAAGG TTTCTCAGCA   780
AACTACAGTG TCTTGCAGAG CAGTGTCTCA GAAGATTCA GAAGTATGGA AGCTCTGGGC   840
ATGGAATCAG GAGAAATTCA TCTGACCAG ATCACAGCTT CTTCCCAGTA TAGCACCAAC   900
TGGTCTGCAG AGCGCTCCCG CCTGAACTAC CCTGAGAATG GGTGGACTCC CGGAGAGGAT   960
TCCTACCGAG AGTGGATACA GGTAGACTTG GGCCTTCTGC GCTTTGTCAC GGCTGTCGGG  1020
ACACAGGGCG CCATTTCAAA AGAAACCAAG AGAAATATT ATGTCAAGAC TTACAAGATC  1080
```

FIG. 5-1

```
GAGGTTAGCT CCAACGGGGA AGACTGGATC ACCATAAAAG AAGGAAACAA ACCTGTTCTC    1140
TTTCAGGGAA ACACCAACCC CACAGATGTT GTGGTTGCAG TATTCCCCAA ACCACTGATA    1200
ACTCGATTTG TCCGAATCAA GCCTGCAACT TGGGAAACTG GCATATCTAT GAGATTTGAA    1260
GTATACGGTT GCAAGATAAC AGATTATCCT TGCTCTGGAA TGTTGGGTAT GGTGTCTGGA    1320
CTTATTTCTG ACTCCCAGAT CACATCATCC AACCAAGGAG ACAGAAACTG GATGCCTGAA    1380
AACATCCGCC TGGTAACCAG TCGCTCTGGC TGGGCACTTC CACCCGCACC TCATTCCTAC    1440
ATCAATGAGT GGCTCCAAAT AGACCTGGGG GAGGAGAAGA TCGTGAGGGG CATCATCATT    1500
CAGGGTGGGA AGCACCAGAG GAACAAGGTG TTCATGAGGA AGTTCAAGAT CGGGTACAGC    1560
AACAACGGCT CGGACTGGAA GATGATCATG GATGACAGCA AACGCAAGGC GAAGTCTTTT    1620
GAGGGCAACA ACAACTATGA TACACCTGAG CTCGGGACTT TTCCAGTCTCT CTCCACGCGA    1680
TTCATCAGGA TCTACCCCGA GAGAGCCACT CATGGCGGAC TGGGGCTCAG AATGGAGCTG    1740
CTGGGCTGTG AAGTGGAAGC CCCTACAGCT GGACCACCA CTCCCAACGG GAACTTGGTG    1800
GATGAATGTG ATGACGACCA GGCCAACTGC CACAGTGGAA CAGGTGATGA CTTCCAGCTC    1860
ACAGGTGGCA CCACTGTGCT GGCCACAGAA AAGCCCACG TCATAGACAG CACCATACAA    1920
TCAGAGTTTC CAACATATGG TTTTAACTGT GAATTGGCT GGGCTCTCA CAAGACCTTC    1980
TGCCACTGGG AACATGACAA TCACGTGCAG CTCAAGTGA GTGTGTTGAC CAGCAAGACG    2040
GGACCCATTC AGGAGATGGC AGGAGATGGC AACTTCATCT ATTCCCAAGC TGACGAAAAT    2100
CAGAAGGGCA AAGTGGCTCG CCTGGTGAGC CCTGTGGTTT ATCCCAGAA CTCTGCCCAC    2160
TGCATGACCT TCTGGTATCA CATGTCTGGA TCCCACGTCG GCACACTCAG GGTCAAACTG    2220
CGTACCAGA AGCCAGAGGA GTACGATCAG CTGGTCTGGA TGGCCATTGG ACACCAAGGT    2280
GACCACTGGA AGGAAGGGCG TGTCTTGCTC CACAGTCTC TGAAACTTTA TCAGTTGATT    2340
TTCGAGGGCG AAATCGGAAA AGGAAACCTT GGTGGATTG CTGTGGATGA CATTAGTATT    2400
AATAACCACA TTTCACAAGA AGATTGTGCA AACCAGCAG ACCTGGATAA AAGAACCCA    2460
GAAATTAAAA TTGATGAAAC AGGGAGCACG CCAGGATACG AAGGTGAAGG AGAAGGTGAC    2520
AAGAACATCT CCAGGAAGCC AGGCAATGTG TTGAAGACCT TAGAACCCAT CCTCATCACC    2580
ATCATAGCCA TGAGCGCCCT GGGGGTCCTC CTGGGGGCTG TCTGTGGGGT CGTGCTGTAC    2640
TGTGCCTGTT GGCATAATGG GATGTCAGAA AGAACTTGT CTGCCCTGGA GAACTATAAC    2700
TTTGAACTTG TGGATGGTGT GAAGTTGAAA AAGACAAAC TGAATACACA TGAATACTTAT    2760
TCGGAGGCAT GA                                                       2772
```

FIG. 5-2

```
ATGGAGAGGG GGCTGCCGTT GCTGTGCGCC ACGCTCGCCC TTGCCCTCGC CCTGGGGGCT    60
TTCCGCAGCG ATAAATGTGG CGGGACTATA AAAATTGAAA ACCCGGGGTA CCTTACATCT   120
CCCGGCTACC CTCATTCTTA CCATCCAAGT GAGAAATGTG AATGGCTAAT CCAAGCTCCG   180
GAGCCCTACC AGAGAATCAT GATCAACTTC AACCCACATT TCGATTTGGA GGACAGAGAC   240
TGCAAGTATG ACTATGTGGA AGTGATCGAT GGAGAGAATG AAGGTGCCCG CCTGTGGGGG   300
AAGTTCTGTG GGAAGATCGC ACCTTCACCT GTGGTGTCTT CAGGGCCATT TCTCTTCATC   360
AAATTTGTCT CTGACTATGA GACCCACGGG GCAGGATTTT CCATCCGCTA TGAAATCTTC   420
AAGAGAGGGC CCGAATGTTC TCAGAACTAT ACAGCACCTA CTGGAGTGAT AAAGTCCCCT   480
GGGTTCCCTG AAAAATACCC CAACAGCTTG GAGTGCACCT ACATCATCTT TGCACCAAAG   540
ATGTCTAGA TAATCCTAGA GTTTGAAAGT TTTGACCTGG AGCAAGACTC AAATCCTCCC   600
GGAGGAATGT TCTGTCGCTA TGACCGGCTG GAGATCTGGG ATGGATTCCC TGAAGTTGGC   660
CCTCACATTG GGCGTTACTG TGGGCAGAAA ACTCCCTGGC GGATCCGCTC CTCTTCAGGC   720
ATTCTATCCA TGGTCTTCTA CACTGACAGC GCAATAGCAA AGGAAGGTTT CTCAGCCAAC   780
TACAGCGTGC TGCAGAGCAG CATCTCTGAA GATTTCAAGT GTATGGAGGC TCTGGGCATG   840
GAATCTGGAG AGATCCATTC TGACCAGATC ACTGCCATCTT CCCAGTATGG TACCAACTGG   900
TCTGTTGAGC GCTCCCGCCT GAACTACCCT GAAAACGGGT GGACACCAGG AGAGGACTCC   960
TACAGGGAGT GGATCCAGGT GGACTTGGGC CTCCTGCGAT TCGTTACTGC TGTGGGGACA  1020
CAGGGTGCCA TTTCCAAGGA AACCAAGAAG AAATATTATG TCAAGACTTA CAGAGTAGAC  1080
ATCAGCTCCA ACGGAGAGGA CTGGATCACC CTGAAGGAGG GAAATAAAGC CATTATCTTT  1140
CAGGGAAACA CCAATCCCAC TGGATGTGTC TTTGGAGTTT TCCCCAAACC ACTGATAACT  1200
CGATTTGTCC GAATCAAACC TGCATCCTGG GAAACTGGAA TATCTATGAG ATTTGAAGTT  1260
TATGGCTGCA AGATAACAGA TTACCCTTGC TCTGGAATGT TGGGCATGGT GTCTGGACTT  1320
ATTTCAGACT CCCAGATTAC AGCATCCAAC CAAGGAGACA GGAACTGGAT GCCAGAAAAC  1380
ATCCGCCTGG TGACCAGTCG AACCGGCTGG GCCCTGCCAC CCTCACCCCA CCCATACATC  1440
AATGAATGGC TCCAAGTGGA CTTGGGAGAT GAGAAGATAG TAAGAGGTGT CATCATTCAA  1500
GGTGGAAGC ACCGAGAAAA CAAAGTGTTC ATGAGGAAGT TCAAGATGCG CTACAGTAAC  1560
AATGGTTCTG ACTGGAAAAT GATCATGGAT GACGCAAGC GCAAGGCTAA GTCTTTTGAA  1620
GGCAACAACA ACTATGACAC ACCTGAGCTC CGGGCCTTTA CACCTCTCTC CACAAGATTC  1680
```

FIG. 6-1

```
ATCAGGATCT ACCCCGAGAG AGCCACACAT AGTGGGCTCG GACTGAGGAT GGAGCTACTG    1740
GGCTGTGAAG TAGAAGTGCC TACAGCTGGA CCCACGACAC CCAATGGGAA CCCCGTGGAC    1800
GAGTGTGACG ATGACCAGGC CAACTGCCAC AGTGGCACAG GTGATGACTT CCAGCTCACA    1860
GGAGGCACCA CTGTCCTGC  CACAGAGAAG CCCACCATTA TAGACAGCAC CATCCAATCA    1920
GAGTTCCCGA CATACGGTTT TAACTGCGAG TTTGGCTGGG GCTCTCACAA GACATTCTGC    1980
CACTGGGAAC ATGACAGCCA CGCGCAGCTC AGGTGGAGG  TGCTGACCAG CAAGACGGGG    2040
CCCATTCAGG ACCACACAGG AGATGGCAAC TTCATCTATT CCCAAGCTGA TGAAAATCAG    2100
AAAGGCAAAG TAGCCCGCCT GGTGAGCGCCT GTGGTCTATT CCCAGAGTTC TGCCCACTGC    2160
ATGACCTTCT GGTATCACAT GTCCGGCTCT CATGTGGGTA CACTGAGGGT CAAACTGCAC    2220
TACCAGAAGC CAGAGAATA  TGATCAACTG GTCTGGATGG TGGTCGGGCA CCAAGAGAC    2280
CACTGGAAGG AAGGGCGTGT CTTGCTGCAC AAATCTCTGA AACTGTATCA GGTTATTTTT    2340
GAAGGTGAAA TCGGAAAAGG AAACCTCGGT GGGATTGCTG TGGATGATAT CAGTATTAAC    2400
AACCACATTC CTCAGGAGGA CTGTCAAAA  CCAACAGACC TAGATAAAAA GAACACAGAA    2460
ATTAAAATAG ATGAAACAGG GAGCACCCCA GGATATGAAG AAGGGAAAGG CGAACAGAAC    2520
ATCTCCAGA  AGCCAGCAA  TGTGCTTAAG ACCCTGGACC CCATCCTGAT CACCATCATA    2580
GCCATGAGTG GCTCCTGGGT GCTCCTGTG  GAGTTGTGCT GTACTGTGCC    2640
TGTTGGCACA ATGGGATGTC GGAAAGGAAC TGGAGAACTA TAACTTTGAA              2700
CTTGTGGATG GTGTAAAGTT GAAAAAAGAT AACTGAACC  CACACAGTAA TTACTCAGAG    2760
GCGTGA                                                              2766
```

FIG. 6-2

```
TTTTTTTTTT TTTTTTTTT TTTTTTTTTT TTTTTCCTCC TTCTCTCTCT TCCTGAGACA      60
TGGCCCGGGC AGTGGCTCCT GGAAGAGGAA CAAGTGTGGG AAAAGGAGA GGAAATCGGA     120
GCTAAATGAC AGGATGCAGG CGACTTGAGA CACAAAAAGA GAAGCGCTTC TCCGAATTC     180
AGGCATTGCC TCGCCGCTAG CCTTCCCCGC CAAGACCCGC TGAGGATTTT ATGGTTCTTA    240
GGCGGACTTA AGAGCGTTTC GGATTGTTAA GATTATCGTT TGCTGGTTTT TCGTCCGCGC    300
AATCGTGTTC TCCTGCGGCT GCCTGGGGAC TGGCTTGGCG AAGGAGGATG GAGAGGGGC    360
TGCCGTTGCT GTGCGCCACG CTCGCCCTTG CCCTCGCCCT GGCGGGCGCT TTCCGCAGCG    420
ACAAATGTGG CGGGACCATA AAAATCGAAA ACCCAGGGTA CCTCACATCT CCCGGTTACC    480
CTCATTCTTA CCATCCAAGT GAGAAGTGTG AATGGCTAAT CCAAGCTCCG GAACCCTACC    540
AGAGAATCAT AATCAACTTC TCGATTTGA GGACAGAGAC TGCAAGTATG     600
ACTACGTGGA AGTAATTGAT GGGGAGAATG AAGGCGGGCC CCTGTGGGGG AAGTTCTGTG    660
GGAAGATTGC ACCTTCTCCT GTGGTGTCTT CAGGGCCCCTT TCTCTTCATC AAATTTGTCT    720
CTGACTATGA GACACATGGG GCAGGGTTTT CCATCCGCTA TGAAATCTTC AAGAGAGGGC    780
CCGAATGTTC TCAGAACTAT ACAGCACCTA CTGGAGTGAT AAAGTCCCCT GGGTTCCCTG    840
AAAAATACCC CAACTGCTG GAGTGCACCT ACATCATCTT TGCACCAAAG ATGTCTGAGA    900
TAATCCTGGA GTTTGAAAGT TTTGACCTGG AGCAAGACTC GAATCCTCCC GGAGGAATGT    960
TCTGTCGCTA TGACCGGCTG GAGATCTGGG ATGGATTCCC TGAAGTTGGC CCTCACATTG   1020
GGCGTTATTG TGGGCAGAAA ACTCCTGGCC GGATCCGCTC CTCTTCAGGC GTTCTATCCA    1080
TGGTCTTTTA CACTGACAGC GCAATAGCAA AAGAAGGTTT CTCAGCCAAC TACAGTGTGC    1140
TACAGAGCAG CATCTCTGAA GATTTTAAGT GTATGGAGGC TCTGGGCATG GAATCTGGAG    1200
AGATCCATTC TGATCAGATC ACTGCATCTT CACAGTATGG TACCAACTGG TCTGTAGAGC    1260
GCTCCCGCCT GAACTACCCT GAAAATGGGT GGACTCCAGG AGAAGACTCC TACAAGGAGT    1320
GGATCCAGGT GGACTTGGGC CTCCTGCGAT TGTTACTGC TGTAGGGACA CAGGGTGCCA    1380
TTTCCAAGGA AACCAAGAAG AAATATTATG TCAAGACTTA CAGAGTAGAC ATCAGTCCA    1440
ACGGAGAGGA CTGGATCTCC CTGAAAGAGG GAAATAAAGC CATTATCTTT CAGGAAAACA    1500
CCAACCCCAC AGATGTTGTC TTAGGAGTTT TCTCCAAACC ACTGATAACT CGATTGTTCC    1560
GAATCAAACC TGTATCCTGG GAAACTGGTA TATCTATGAG ATTTGAAGTT TATGGCTGCA    1620
AGATAACAGA TTATCCTTGC TCTGGAATGT TGGGCATGGT GTCTGGACTT ATTTCAGACT    1680
CCCAGATTAC AGCATCCAAT CAAGCCGACA GGAATTGGAT GCCAGAAAAC ATCCGTCTGG   1740
```

FIG. 7-1

```
TGACCAGTCG TACCGGCTGG GCACTGCCAC CCTCACCCCA CCCATACACC AATGAATGGC  1800
TCCAAGTGGA CCTGGGAGAT GAGAAGATAG TAAGAGGTGT CATCATTCAG GGTGGGAAGC  1860
ACCGAGAAAA CAAGGTGTTC ATGAGGAAGT TCAAGATCGC CTATAGTAAC AATGGCTCTG  1920
ACTGGAAAAC TATCATGGAT GACAGCAAGC GCAAGGCTAA GTCGTTCGAA GGCAACAACA  1980
ACTATGACAC ACCTGAGCTT CGGACGTTTT CACCTCTCTC CACAAGGTTC ATCAGGATCT  2040
ACCCTGAGAG AGCCACACAC AGTGGGCTTG GGCTGAGGAT GGAGCTACTG GGCTGTGAAG  2100
CATACGGTTT TAACTGCGAG TTTGCTGGG  GCTCTCACAA GACATTCTGC CACTGGGAGC  2340
ATGACAGCCA TGCACAGCTC AGTGGAGTG  TGCTGACCAG CAAGACAGGG CCGATTCAGG  2400
ACCATACAGG AGATGGCAAC TTCATCTATT CCCAAGCTGA TGAAAATCAG AAAGGCAAAG  2460
TAGCCCGCCT GGTGAGCCCT GTGGTCTATT CCCAGAGCTC TGCCCACTGT ATGACCTTCT  2520
GGTATCACAT GTCCGGCTCT CATGTGGGTA CACTGAGGGT CAAACTACGC TACCAGAAGC  2580
CAGAGGAATA TGATCAACTG GTCTGATGG  TGGTTGGGCA CCAAGGAGAC CACTGGAAAG  2640
AAGGACGTGT CTTGCTGCAC AAATCTGCAC AACTATATCA GGTTATTTTT GAAGGTGAAA  2700
TCGGAAAAGG AAACCTTGGT GGAATTGCTG TGGATGATAT CAGTATTATAC AACCATATTT  2760
CTCAGGAAGA CTGTGCAAAA CCAACAGACC TAGATAAAAA GAACACAGAA ATTAAAATTG  2820
ATGAAACAGG GAGCACTCCA GGATATGAAG GAGAAGGGGA AGGTGACAAG AACATCTCCA  2880
GGAAGCCAGG CAATGTGCTT AAGACCCTGG ATCCCATCCT GATCACCATC ATAGCCATGA  2940
GTGCCCCTGG AGTACTCCTG GGTGCAGTCT GTGGAGTTGT GCTGTACTGT GCCTGTTGGC  3000
ACAATGGGAT GTCAGAAAGG AACCTATCTG CCCTGGAGAA CTATAACTTT GAACTTGTGG  3060
ATGGTGTAAA GTTGAAAAAA GATAAACTGA ACCCACACAG TAATTACTCA GAGGCGTGAA  3120
GGCACGGAGC TGGAGGGAAC AAGGGAGGAG CACGGCAGGA GAACAGGTGG AGGCATGGGG  3180
ACTCTGTTAC TCTGCTTTCA CTGTAAGCTG GGACTCTGTT ACTCCGCTTT ACTCCGCTTT  3240
CACTGTAAGC TCGGAAGGGC ATCCACGATG CCATGCCAGG CTTTTCTCAG GAGCTTCAAT  3300
GAGCGTCACC TACAGACACA AGCAGGTGAC TGCGGTAACA ACAGGAATCA TGTACAAGCC  3360
TGCTTTCTTC TCTTGGTTTC ATTTGGGTAA TCAGAAGCCA TTTGAGACCA AGTGTGACTG  3420
ACTTCATGGT TCATCCTACT AGCCCCCTTT TTTCCTCTCT TTCTCCTTAC CCTGGTGTGG  3480
ATTCTTCTCG GAAACTGCAA AATCCAAGAT GCTGGCACTA GGGTTATTC  AGTGGGCCCT  3540
TTTGATGGAC ATGTGACCTG TAGCCCAGTG CCCAGAGCAT ATTATCATAA CCACATTTCA  3600
GGGGACGCCA AGTCCATCC  ACCTTTGCAT CGTCTACCTGC AGCCAGCACA GG          3652
```

FIG. 7-2

SEQUENCE LISTING

```
<160> NUMBER OF SEQ ID NOS: 35

<210> SEQ ID NO 1
<211> LENGTH: 20
<212> TYPE: DNA
<213> ORGANISM: Human

<400> SEQUENCE: 1
gagcggcagc cccctctcca                                               20

<210> SEQ ID NO 2
<211> LENGTH: 20
<212> TYPE: DNA
<213> ORGANISM: Human

<400> SEQUENCE: 2
cgagcacggc gcagaggagc                                               20

<210> SEQ ID NO 3
<211> LENGTH: 20
<212> TYPE: DNA
<213> ORGANISM: Human

<400> SEQUENCE: 3
ggacgagggc gagcacggcg                                               20

<210> SEQ ID NO 4
<211> LENGTH: 20
<212> TYPE: DNA
<213> ORGANISM: Human

<400> SEQUENCE: 4
tgggtccgga gcctgaatca                                               20
```

```
<210> SEQ ID NO 5
<211> LENGTH: 20
<212> TYPE: DNA
<213> ORGANISM: Human

<400> SEQUENCE: 5
tttttcaggg aatccggggg                                           20

<210> SEQ ID NO 6
<211> LENGTH: 20
<212> TYPE: DNA
<213> ORGANISM: Human

<400> SEQUENCE: 6
gggtagttca ggcgggagcg                                           20

<210> SEQ ID NO 7
<211> LENGTH: 20
<212> TYPE: DNA
<213> ORGANISM: Human

<400> SEQUENCE: 7
aatggcgccc tgtgtcccga                                           20

<210> SEQ ID NO 8
<211> LENGTH: 20
<212> TYPE: DNA
<213> ORGANISM: Human

<400> SEQUENCE: 8
gtgcccagcc agagcgactg                                           20

<210> SEQ ID NO 9
<211> LENGTH: 20
<212> TYPE: DNA
<213> ORGANISM: Human

<400> SEQUENCE: 9
tgaggtgcgg gtggaagtgc                                           20

<210> SEQ ID NO 10
<211> LENGTH: 20
<212> TYPE: DNA
<213> ORGANISM: Human

<400> SEQUENCE: 10
gtgccgacgt gggacccaga                                           20

<210> SEQ ID NO 11
<211> LENGTH: 20
<212> TYPE: DNA
<213> ORGANISM: Human

<400> SEQUENCE: 11 gaccccccagg gcactcatgg                                          20

<210> SEQ ID NO 12
<211> LENGTH: 20
<212> TYPE: DNA
<213> ORGANISM: Human

<400> SEQUENCE: 12
cgaccccaca gacagccccc                                           20
```

-continued

<210> SEQ ID NO 13
<211> LENGTH: 20
<212> TYPE: DNA
<213> ORGANISM: Human

<400> SEQUENCE: 13
tctctgtcct ccaaatcgaa                                               20

<210> SEQ ID NO 14
<211> LENGTH: 20
<212> TYPE: DNA
<213> ORGANISM: Human

<400> SEQUENCE: 14
tgcttcccac cctgaatgat                                               20

<210> SEQ ID NO 15
<211> LENGTH: 20
<212> TYPE: DNA
<213> ORGANISM: Human

<400> SEQUENCE: 15
tgggaataga tgaagttgcc                                               20

<210> SEQ ID NO 16
<211> LENGTH: 20
<212> TYPE: DNA
<213> ORGANISM: Human

<400> SEQUENCE: 16
tcctctggct ctggtagcg                                                20

<210> SEQ ID NO 17
<211> LENGTH: 20
<212> TYPE: DNA
<213> ORGANISM: Human

<400> SEQUENCE: 17
aggtttcctt ttccgatttc                                               20

<210> SEQ ID NO 18
<211> LENGTH: 20
<212> TYPE: DNA
<213> ORGANISM: Human

<400> SEQUENCE: 18
gtgctccctg tttcatcaat                                               20

<210> SEQ ID NO 19
<211> LENGTH: 20
<212> TYPE: DNA
<213> ORGANISM: Human

<400> SEQUENCE: 19
cattgcctgg cttcctggag                                               20

<210> SEQ ID NO 20
<211> LENGTH: 20
<212> TYPE: DNA
<213> ORGANISM: Human

<400> SEQUENCE: 20

| | |
|---|---|
| cccagggcac tcatggctat | 20 |

<210> SEQ ID NO 21
<211> LENGTH: 20
<212> TYPE: DNA
<213> ORGANISM: Human

<400> SEQUENCE: 21

| | |
|---|---|
| gctgagaaac cttcttttgc | 20 |

<210> SEQ ID NO 22
<211> LENGTH: 20
<212> TYPE: DNA
<213> ORGANISM: Human

<400> SEQUENCE: 22

| | |
|---|---|
| aacatctgtg gggttggtgt | 20 |

<210> SEQ ID NO 23
<211> LENGTH: 20
<212> TYPE: DNA
<213> ORGANISM: Human

<400> SEQUENCE: 23

| | |
|---|---|
| tcggacaaat cgagttatca | 20 |

<210> SEQ ID NO 24
<211> LENGTH: 20
<212> TYPE: DNA
<213> ORGANISM: Human

<400> SEQUENCE: 24

| | |
|---|---|
| caacattcca gagcaaggat | 20 |

<210> SEQ ID NO 25
<211> LENGTH: 20
<212> TYPE: DNA
<213> ORGANISM: Human

<400> SEQUENCE: 25

| | |
|---|---|
| cgatcttgaa cttcctcatg | 20 |

<210> SEQ ID NO 26
<211> LENGTH: 20
<212> TYPE: DNA
<213> ORGANISM: Human

<400> SEQUENCE: 26

| | |
|---|---|
| cctgtgagct ggaagtcatc | 20 |

<210> SEQ ID NO 27
<211> LENGTH: 20
<212> TYPE: DNA
<213> ORGANISM: Human

<400> SEQUENCE: 27

| | |
|---|---|
| catgtgatac cagaaggtca | 20 |

<210> SEQ ID NO 28
<211> LENGTH: 20
<212> TYPE: DNA
<213> ORGANISM: Human

<400> SEQUENCE: 28

-continued

| | |
|---|---|
| ccaacaggca cagtacagca | 20 |

<210> SEQ ID NO 29
<211> LENGTH: 20
<212> TYPE: DNA
<213> ORGANISM: Human

<400> SEQUENCE: 29

| | |
|---|---|
| accatccaca agttcaaagt | 20 |

<210> SEQ ID NO 30
<211> LENGTH: 20
<212> TYPE: DNA
<213> ORGANISM: Human

<400> SEQUENCE: 30

| | |
|---|---|
| accacagggc tcaccaggcg | 20 |

<210> SEQ ID NO 31
<211> LENGTH: 20
<212> TYPE: DNA
<213> ORGANISM: Human

<400> SEQUENCE: 31

| | |
|---|---|
| cgctcccgcc tgaactaccc | 20 |

<210> SEQ ID NO 32
<211> LENGTH: 20
<212> TYPE: DNA
<213> ORGANISM: Human

<400> SEQUENCE: 32

| | |
|---|---|
| tcccaccctg aatgatgatg | 20 |

<210> SEQ ID NO 33
<211> LENGTH: 2772
<212> TYPE: DNA
<213> ORGANISM: Human

<400> SEQUENCE: 33

| | |
|---|---|
| atggagaggg ggctgccgct cctctgcgcc gtgctcgccc tcgtcctcgc cccggccggc | 60 |
| gcttttcgca acgatgaatg tggcgatact ataaaaattg aaagccccgg gtaccttaca | 120 |
| tctcctggtt atcctcattc ttatcaccca agtgaaaaat gcgaatggct gattcaggct | 180 |
| ccggacccat accagagaat tatgatcaac ttcaaccctc acttcgattt ggaggacaga | 240 |
| gactgcaagt atgactacgt ggaagtcttc gatggagaaa atgaaaatgg acattttagg | 300 |
| ggaaagttct gtggaaagat agcccctcct cctgttgtgt cttcagggcc atttctttt | 360 |
| atcaaatttg tctctgacta cgaaacacat ggtgcaggat tttccatacg ttatgaaatt | 420 |
| ttcaagagag gtcctgaatg ttcccagaac tacacaacac ctagtggagt gataaagtcc | 480 |
| cccggattcc ctgaaaaata tcccaacagc cttgaatgca cttatattgt ctttgcgcca | 540 |
| aagatgtcag agattatcct ggaatttgaa agctttgacc tggagcctga ctcaaatcct | 600 |
| ccagggggga tgttctgtcg ctacgaccgg ctagaaatct gggatggatt ccctgatgtt | 660 |
| ggccctcaca ttgggcgtta ctgtggacag aaaacaccag gtcgaatccg atcctcatcg | 720 |
| ggcattctct ccatggtttt ttacaccgac agcgcgatag caaaagaagg tttctcagca | 780 |
| aactacagtg tcttgcagag cagtgtctca gaagatttca atgtatggga agctctgggc | 840 |

-continued

```
atggaatcag gagaaattca ttctgaccag atcacagctt cttcccagta tagcaccaac      900
tggtctgcag agcgctcccg cctgaactac cctgagaatg ggtggactcc cggagaggat      960
tcctaccgag agtggataca ggtagacttg ggccttctgc gctttgtcac ggctgtcggg     1020
acacagggcg ccatttcaaa agaaaccaag aagaaatatt atgtcaagac ttacaagatc     1080
gacgttagct ccaacgggga agactggatc accataaaag aaggaaacaa acctgttctc     1140
tttcagggaa acaccaaccc cacagatgtt gtggttgcag tattcccaa accactgata      1200
actcgatttg tccgaatcaa gcctgcaact tgggaaactg gcatatctat gagatttgaa     1260
gtatacggtt gcaagataac agattatcct tgctctggaa tgttgggtat ggtgtctgga     1320
cttatttctg actcccagat cacatcatcc aaccaaggag acagaaactg gatgcctgaa     1380
aacatccgcc tggtaaccag tcgctctggc tgggcacttc acccgcacc tcattcctac      1440
atcaatgagt ggctccaaat agacctgggg gaggagaaga tcgtgagggg catcatcatt     1500
cagggtggga agcaccgaga gaacaaggtg ttcatgagga agttcaagat cgggtacagc     1560
aacaacggct cggactggaa gatgatcatg gatgacagca acgcaaggc gaagtctttt      1620
gagggcaaca caactatga tacacctgag ctgcggactt ttccagctct ctccacgcga      1680
ttcatcagga tctaccccga gagagccact catggcggac tggggctcag aatggagctg     1740
ctgggctgtg aagtggaagc ccctacagct ggaccgacca ctcccaacgg gaacttggtg     1800
gatgaatgtg atgacgacca ggccaactgc cacagtggaa caggtgatga cttccagctc     1860
acaggtggca ccactgtgct ggccacagaa agcccacgg tcatagacag caccatacaa      1920
tcagagtttc aacatatgg ttttaactgt gaatttggct ggggctctca caagaccttc      1980
tgccactggg aacatgacaa tcacgtgcag ctcaagtgga gtgtgttgac cagcaagacg     2040
ggacccattc aggatcacac aggagatggc aacttcatct attcccaagc tgacgaaaat     2100
cagaagggca agtggctcg cctggtgagc cctgtggttt attcccagaa ctctgcccac     2160
tgcatgacct tctggtatca catgtctggg tcccacgtcg gcacactcag ggtcaaactg     2220
cgctaccaga agccgagga gtacgatcag ctggtctgga tggccattgg acaccaaggt     2280
gaccactgga aggaagggcg tgtcttgctc cacaagtctc tgaaactta tcaggtgatt      2340
ttcgagggcg aaatcggaaa aggaaaccctt ggtgggattg ctgtggatga cattagtatt     2400
aataaccaca tttcacaaga agattgtgca aaaccagcag acctggataa aaagaaccca     2460
gaaattaaaa ttgatgaaac agggagcacg ccaggatacg aaggtgaagg agaaggtgac     2520
aagaacatct ccaggaagcc aggcaatgtg ttgaagacct tagaacccat cctcatcacc     2580
atcatagcca tgagcgccct gggggtcctc ctgggggctg tctgtgggggt cgtgctgtac     2640
tgtgcctgtt ggcataatgg gatgtcagaa agaaacttgt ctgccctgga gaactataac     2700
tttgaacttg tggatggtgt gaagttgaaa aaagacaaac tgaatacaca gagtacttat     2760
tcggaggcat ga                                                         2772
```

<210> SEQ ID NO 34
<211> LENGTH: 2766
<212> TYPE: DNA
<213> ORGANISM: Rat neuropilin

<400> SEQUENCE: 34

```
atggagaggg ggctgccgtt gctgtgcgcc acgctcgccc ttgccctcgc cctgggggct       60
ttccgcagcg ataaatgtgg cggactata aaaattgaaa acccggggta ccttacatct      120
cccggctacc ctcattctta ccatccaagt gagaaatgtg aatggctaat ccaagctccg      180
```

-continued

```
gagccctacc agagaatcat gatcaacttc aacccacatt tcgatttgga ggacagagac    240
tgcaagtatg actatgtgga agtgatcgat ggagagaatg aaggtggccg cctgtggggg    300
aagttctgtg ggaagatcgc accttcacct gtggtgtctt cagggccatt tctcttcatc    360
aaatttgtct ctgactatga gacccacggg gcaggatttt ccatccgcta tgaaatcttc    420
aagagagggc ccgaatgttc tcagaactat acagcaccta ctggagtgat aaagtcccct    480
gggttccctg aaaaatacccc aacagcttg gagtgcacct acatcatctt tgcaccaaag    540
atgtctgaga taatcctaga gtttgaaagt tttgacctgg agcaagactc aaatcctccc    600
ggaggaatgt tctgtcgcta tgaccggctg gagatctggg atggattccc tgaagttggc    660
cctcacattg ggcgttactg tgggcagaaa actcctggcc ggatccgctc ctcttcaggc    720
attctatcca tggtcttcta cactgacagc gcaatagcaa aggaaggttt ctcagccaac    780
tacagcgtgc tgcagagcag catctctgaa gatttcaagt gtatggaggc tctgggcatg    840
gaatctggag agatccattc tgaccagatc actgcatctt cccagtatgg taccaactgg    900
tctgttgagc gctcccgcct gaactaccct gaaaacgggt ggacaccagg agaggactcc    960
tacagggagt ggatccaggt ggacttgggc ctcctgcgat cgttactgc tgtgggggaca   1020 cagggtgcca tttccaagga aaccaagaag aaatattatg tcaagactta cagagtagac   1080
atcagctcca acggagagga ctggatcacc ctgaaggagg gaaataaagc cattatcttt   1140
caggaaaaca ccaatcccac ggatgttgtc tttggagttt tccccaaacc actgataact   1200
cgatttgtcc gaatcaaacc tgcatcctgg gaaactggaa tatctatgag atttgaagtt   1260
tatggctgca agataacaga ttacccttgc tctggaatgt tgggcatggt gtctggactt   1320
atttcagact cccagattac agcatccaac caggagacag ggaactggat gccagaaaac   1380
atccgcctgg tgaccagtcg aaccggctgg gccctgccac cctcaccccca cccatacatc   1440 aatgaatggc tccaagtgga cctgggagat gagaagatag taagaggtgt catcattcaa   1500
ggtgggaagc accgagaaaa caaagtgttc atgaggaagt tcaagatcgc ctacagtaac   1560
aatggttctg actggaaaat gatcatggat gacagcaagc gcaaggctaa gtctttttgaa   1620 ggcaacaaca actatgacac acctgagctc cgggcccttta cacctctctc cacaagattc   1680
atcaggatct accccgagag agccacacat agtgggctcg gactgaggat ggagctactg   1740
ggctgtgaag tagaagtgcc tacagctgga cccacgacac ccaatgggaa ccccgtggac   1800
cagtgtgacg atgaccaggc caactgccac agtggcacag gtgatgactt ccagctcaca   1860
ggaggcacca ctgtcctggc cacagagaag cccaccatta tagacagcac catccaatca   1920
gagttcccga catacggttt taactgcgag tttggctggg gctctcacaa gacattctgc   1980
cactgggaac atgacagcca cgcgcagctc aggtggaggg tgctgaccag caagacgggg   2040
cccattcagg accacacagg agatggcaac ttcatctatt cccaagctga tgaaaatcag   2100
aaaggcaaag tagcccgcct ggtgagccct gtggtctatt cccagagttc tgcccactgc   2160
atgaccttct ggtatcacat gtccggctct catgtgggta cactgagggt caaactgcac   2220
taccagaagc cagaggaata tgatcaactg gtctggatgg tggtcgggca ccaaggagac   2280
cactggaagg aagggcgtgt cttgctgcac aaatctctga aactgtatca ggttatttt   2340 gaaggtgaaa tcggaaaagg aaacctcggt gggattgctg tggatgatat cagtattaac   2400
aaccacattc ctcaggagga ctgtgcaaaa ccaacagacc tagataaaaa gaacacagaa   2460
attaaaatag atgaaacagg gagcacccca ggatatgaag aagggaaagg cgacaagaac   2520
```

-continued

| | |
|---|---|
| atctccagga agccaggcaa tgtgcttaag accctggacc ccatcctgat caccatcata | 2580 |
| gccatgagtg ccctgggggt gctcctgggt gcagtctgtg gagttgtgct gtactgtgcc | 2640 |
| tgttggcaca atgggatgtc ggaaaggaac ctatctgccc tggagaacta aactttgaa | 2700 |
| cttgtggatg gtgtaaagtt gaaaaaagat aaactgaacc cacacagtaa ttactcagag | 2760 |
| gcgtga | 2766 |

<210> SEQ ID NO 35
<211> LENGTH: 3652
<212> TYPE: DNA
<213> ORGANISM: Mouse

<400> SEQUENCE: 35

| | |
|---|---|
| tttttttttt tttttttttt tttttttttt ttttcctcc ttcttcttct tcctgagaca | 60 |
| tggcccgggc agtggctcct ggaagaggaa caagtgtggg aaagggaga ggaaatcgga | 120 |
| gctaaatgac aggatgcagg cgacttgaga cacaaaaaga gaagcgcttc tcgcgaattc | 180 |
| aggcattgcc tcgccgctag ccttccccgc caagacccgc tgaggatttt atggttctta | 240 |
| ggcggactta agagcgtttc ggattgttaa gattatcgtt tgctggtttt tcgtccgcgc | 300 |
| aatcgtgttc tcctgcggct gcctggggac tggcttggcg aaggaggatg gagagggggc | 360 |
| tgccgttgct gtgcgccacg ctcgcccttg ccctcgccct ggcgggcgct ttccgcagcg | 420 |
| acaaatgtgg cggaccata aaaatcgaaa acccagggta cctcacatct cccggttacc | 480 |
| ctcattctta ccatccaagt gagaagtgtg aatggctaat ccaagctccg gaaccctacc | 540 |
| agagaatcat aatcaacttc aacccacatt tcgatttgga ggacagagac tgcaagtatg | 600 |
| actacgtgga agtaattgat ggggagaatg aaggcggccg cctgtggggg aagttctgtg | 660 |
| ggaagattgc accttctcct gtggtgtctt cagggccctt tctcttcatc aaatttgtct | 720 |
| ctgactatga gacacatggg gcagggtttt ccatccgcta tgaaatcttc aagagagggc | 780 |
| ccgaatgttc tcagaactat acagcaccta ctggagtgat aaagtccccct gggttccctg | 840 |
| aaaaatacc caactgcttg gagtgcacct acatcatctt tgcaccaaag atgtctgaga | 900 |
| taatcctgga gttgaaagt tttgacctgg agcaagactc gaatcctccc ggaggaatgt | 960 |
| tctgtcgcta tgaccggctg agatctggga atggattccc tgaagttggc cctcacattg | 1020 |
| ggcgttattg tgggcagaaa actcctggcc ggatccgctc ctcttcaggc gttctatcca | 1080 |
| tggtcttta cactgacagc gcaatagcaa aagaaggttt ctcagccaac tacagtgtgc | 1140 |
| tacagagcag catctctgaa gatttaagt gtatggaggc tctgggcatg gaatctggag | 1200 |
| agatccattc tgatcagatc actgcatctt cacagtatgg taccaactgg tctgtagagc | 1260 |
| gctcccgcct gaactaccct gaaaatgggt ggactccagg agaagactcc tacaaggagt | 1320 |
| ggatccaggt ggacttgggc ctcctgcgat tcgttactgc tgtagggaca cagggtgcca | 1380 |
| tttccaagga aaccaagaag aaatattatg tcaagactta cagagtagac atcagctcca | 1440 |
| acggagagga ctggatctcc ctgaaagagg gaaataaagc cattatcttt caggggaaaca | 1500 |
| ccaacccac agatgttgtc ttaggagttt tctccaaacc actgataact cgatttgtcc | 1560 |
| gaatcaaacc tgtatcctgg gaaactggta tatctatgag atttgaagtt tatggctgca | 1620 |
| agataacaga ttatccttgc tctggaatgt tgggcatggt gtctggactt atttcagact | 1680 |
| cccagattac agcatccaat caagccgaca ggaattggat gccagaaaac atccgtctgg | 1740 |
| tgaccagtcg taccgctgg gcactgccac cctcaccca ccatacacc aatgaatggc | 1800 |
| tccaagtgga cctgggagat gagaagatag taagaggtgt catcattcag gtgggaagc | 1860 |

-continued

```
accgagaaaa caaggtgttc atgaggaagt tcaagatcgc ctatagtaac aatggctctg    1920
actggaaaac tatcatggat gacagcaagc gcaaggctaa gtcgttcgaa ggcaacaaca    1980
actatgacac acctgagctt cggacgtttt caccctctctc cacaaggttc atcaggatct   2040
accctgagag agccacacac agtgggcttg ggctgaggat ggagctactg ggctgtgaag    2100
tggaagcacc tacagctgga ccaaccacac ccaatgggaa cccagtgcat gagtgtgacg    2160
acgaccaggc caactgccac agtggcacag gtgatgactt ccagctcaca ggaggcacca    2220
ctgtcctggc cacagagaag ccaaccatta tagacagcac catccaatca gagttcccga    2280
catacggttt taactgcgag tttggctggg gctctcacaa gacattctgc cactgggagc    2340
atgacagcca tgcacagctc aggtggagtg tgctgaccag caagacaggg ccgattcagg    2400
accatacagg agatggcaac ttcatctatt cccaagctga tgaaaatcag aaaggcaaag    2460
tagcccgcct ggtgagccct gtggtctatt cccagagctc tgcccactgt atgaccttct    2520
ggtatcacat gtccggctct catgtgggta cactgagggt caaactacgc taccagaagc    2580
cagaggaata tgatcaactg gtctggatgg tggttgggca ccaaggagac cactggaaag    2640
aaggacgtgt cttgctgcac aaatctctga actatatca ggttatttttt gaaggtgaaa    2700
tcggaaaagg aaaccttggt ggaattgctg tggatgatat cagtattaac aaccatattt    2760
ctcaggaaga ctgtgcaaaa ccaacagacc tagataaaaa gaacacagaa attaaaattg    2820
atgaaacagg gagcactcca ggatatgaag gagaagggga aggtgacaag aacatctcca    2880
ggaagccagg caatgtgctt aagaccctgg atcccatcct gatcaccatc atagccatga    2940
gtgccctggg agtactcctg ggtgcagtct gtggagttgt gctgtactgt gcctgttggc    3000
acaatgggat gtcagaaagg aacctatctg ccctggagaa ctataacttt gaacttgtgg    3060
atggtgtaaa gttgaaaaaa gataaactga acccacagag taattactca gaggcgtgaa    3120
ggcacggagc tggagggaac aagggaggag cacggcagga aacaggtgg aggcatgggg    3180
actctgttac tctgctttca ctgtaagctg ggaagggcgg ggactctgtt actccgcttt    3240
cactgtaagc tcggaagggc atccacgatg ccatgccagg cttttctcag gagcttcaat    3300
gagcgtcacc tacagacaca agcaggtgac tgcggtaaca acaggaatca tgtacaagcc    3360
tgctttcttc tcttggtttc atttgggtaa tcagaagcca tttgagacca agtgtgactg    3420
acttcatggt tcatcctact agccccctttt tttcctctct ttctccttac cctgtggtgg    3480
attcttctcg gaaactgcaa aatccaagat gctggcacta ggcgttattc agtgggccct    3540
tttgatggac atgtgacctg tagcccagtg cccagagcat attatcataa ccacatttca    3600
ggggacgcca acgtccatcc acctttgcat cgctacctgc agcgagcaca gg            3652
```

NEUROPILIN ANTISENSE OLIGONUCLEOTIDE SEQUENCES AND METHODS OF USING SAME TO MODULATE CELL GROWTH

REFERENCE TO RELATED APPLICATIONS

This application claims priority to U.S. Provisional Application Ser. No. 60/082,791 filed Apr. 23, 1998, which application is incorporated herein by reference in its entirety.

BACKGROUND OF THE INVENTION

1. Field of the Invention

This invention relates to oligonucleotides that are complementary to mammalian neuropilin (or $VEGF_{165}R$) mRNA which oligonucleotides modulate cell growth in mammals. This invention is also related to methods of using such compounds in inhibiting the growth of tumor cells in mammals and to inhibit angiogenesis in mammals. This invention also relates to pharmaceutical compositions comprising a pharmaceutically acceptable excipient and an effective amount of a compound of this invention.

REFERENCES

The following publications, patent applications and patents are cited in this application as superscript numbers:

1. Tischer, E., et al., "The human gene for vascular endothelial growth factor. Multiple protein forms are encoded through alternative exon splicing," *J Biol Chem.* 266: 11947–54, (1991).
2. Poltorak, Z., et al., "$VEGF_{145}$, a secreted vascular endothelial growth factor isoform that binds to extracellular matrix", *J Biol Chem.* 272: 7151–8, 1997.
3. Terman, B. I., et al., "Identification of the KDR tyrosine kinase as a receptor for vascular endothelial cell growth factor", *Biochem Biophys Res Commun.* 187: 1579–86, 1992.
4. Millauer, B., et al., "High affinity VEGF binding and developmental expression suggest Flk-1 as a major regulator of vasculogenesis and angiogenesis", *Cell.* 72: 835–46, 1993.
5. Shibuya, M., et al., "Nucleotide sequence and expression of a novel human receptor-type tyrosine kinase gene (flt) closely related to the fms family", *Oncogene.* 5: 519–24, 1990.
6. de Vries, C., et al., "The fms-like tyrosine kinase, a receptor for vascular endothelial growth factor", *Science.* 255: 989–91, 1992.
7. Kawakami, A., et al., "Developmentally regulated expression of a cell surface protein, neuropilin, in the mouse nervous system", *J Neurobiol.* 29: 1–17, 1996.
8. Takagi, S., et al., "Expression of a cell adhesion molecule, neuropilin, in the developing chick nervous system", *Dev Biol.* 170: 207–22, 1995.
9. Soker, S., et al., "Neuropilin-1 is expressed by endothelial and tumor cells as an isoform-specific receptor for vascular endothelial growth factor", *Cell.* 92: 735–45, 1998.
10. Soker, S., et al., "Inhibition of vascular endothelial growth factor (VEGF)-induced endothelial cell proliferation by a peptide corresponding to the exon 7-encoded domain of $VEGF_{165}$", *J Biol Chem.* 272: 31582–8, 1997.
11. He, Z. and Tessier-Lavigne, M. "Neuropilin is a receptor for the axonal chemorepellent Semaphorin III", *Cell.* 90: 739–51, 1997.
12. Mitsuhashi, M. "Strategy for designing specific antisense oligonucleotide sequences", *J Gastroenterol.* 32: 282–7, 1997.
13. Alama, A., et al., "Antisense oligonucleotides as therapeutic agents", *Pharmacol Res.* 36: 171–8, 1997.
14. Curcio, L. D., et al., "Oligonucleotides as modulators of cancer gene expression", *Pharmacol Ther.* 74: 317–32, 1997.
15. Brem, S., et al., "Prolonged tumor dormancy by prevention of neovascularization in the vitreous", *Cancer Res.* 36: 2807–12, 1976.
16. Holmgren, L., et al., "Dormancy of micrometastases: balanced proliferation and apoptosis in the presence of angiogenesis suppression", *Nat Med.* 1: 149–53, 1995.
17. Parangi, S., et al., "Antiangiogenic therapy of transgenic mice impairs de novo tumor growth, *Proc Natl Acad Sci USA.* 93: 2002–7, 1996.
18. Choy et al., "Molecular mechanisms of drug resistance involving ribonucleotide reductase: hydroxyurea resistance in a series of clonally related mouse cell lines selected in the presence of increasing drug concentrations" *Cancer Res.* 48:2029–2035 (1988)
19. Fan et al., "Ribonucleotide reductase R2 component is a novel malignancy determinant that cooperates with activated oncogenes to determine transformation and malignant potential" *Proc. Natl. Acad. Sci USA* 93:14036–40 (1996)
20. Huang and Wright, "Fibroblast growth factor mediated alterations in drug resistance and evidence of gene amplification" *Oncogene* 9:491–499 (1994)
21. International Patent Application Publication No. WO99/02556, "Semaphorin Receptors"
22. International Patent Application Publication No. WO99/04263, "Semaphorin Receptor"
23. *Remington's Pharmaceutical Sciences*, Mace Publishing Company, Philadelphia Pa. 17$^{th}$ ed. (1985)
24. Sambrook et al., *Molecular Cloning: A Laboratory Manual*, Cold Spring Harbor Laboratory, New York (1989, 1992)
25. Ausubel et al., *Current Protocols in Molecular Biology*, John Wiley and Sons, Baltimore Md. (1989)
26. Perbal, *A Practical Guide to Molecular Cloning*, John Wiley & Sons, New York (1988)
27. Hurta and Wright, "Malignant transformation by H-ras results in aberrant regulation of ribonucleotide reductase gene expression by transforming growth factor-beta" *J. Cell Biochem* 57:543–556 (1995)
28. International Patent Application Publication No. WO97/21808, "Modified VEGF Antisense Oligonucleotides"
29. Nielsen et al.; *Science* (1991) 354:1497
30. Good and Nielsen; "Inhibition of translation and bacterial growth by peptide nucleic acid targeted to ribosomal RNA", *PNAS USA* (1998) 95:2073–2076
31. Buchardt, deceased, et al., U.S. Pat. No. 5,766,855
32. Buchardt, deceased, et al., U.S. Pat. No. 5,719,262
33. U.S. Pat. No. 5,034,506
34. Altschul, et al. "Basic local alignment search tool", *J. Mol. Biol.* (1990) 215:403–10;
35. Devereux J. et al., "A comprehensive set of sequence analysis programs for the VAX", *Nucleic Acids Res.* (1984) 12:387–395;
36. Chang et al.; Somatic Gene Therapy, CRC Press, Ann Arbor Mich. (1995);
37. Vega et al.; *Gene Targeting*, CRC Press, Ann Arbor Mich. (1995)
38. *Vectors: A Survey of Molecular Cloning Vectors and Their Uses*, Butterworths, Boston Mass. (1988)

39. Sullivan, U.S. Pat. No. 5,225,347
40. U.S. Pat. No. 5,023,252, issued Jun. 11, 1991
41. Feigner et al., U.S. Pat. No. 5,580,859
42. Dreeley et al., *Science,* 258:1650–1654 (1992)
43. Uhimann et al. *Chem Rev.* 90:534–583 (1990)
44. Agrawal et al. *Trends Biotechnol.* 10:152–158 (1992)
45. Smith et al., (1994) *Invest. Ophthalmol. Vis. Sci* 35:101–111
46. Pierce et al., (1995) *Proc. Natl. Acad. Sci USA* 92:905–9

All of the above publications, patent applications and patents are herein incorporated by reference in their entirety to the same extent as if each individual publication, patent application or patent was specifically and individually indicated to be incorporated by reference in its entirety.

2. State of the Art

Proliferation of new capillaries, called angiogenesis or neovascularization, is critical for the transition of a small localized tumor to expand into a large malignant growth. Without the appropriate development of blood supply, tumor growth is dramatically impaired.

Neovascular diseases of the retina such as diabetic retinopathy, retinopathy of prematurity and age-related macular degeneration are a major cause of blindness in the United States and the world. During the course of diabetes mellitus, the retinal vessels undergo changes that result in not only leaky vessels but also vessel drop out resulting in retinal hypoxia. One of the effects of this is neovascularization of the retina resulting in bleeding and retinal detachment. Retinopathy of prematurity is a common cause of blindness in children. The blood vessels of the retina cease to develop into the peripheral retina resulting in ischemia and localized hypoxic conditions as the metabolic demands of the developing retina increase. The resulting hypoxia stimulates the subsequent neovascularization of the retina which can lead to irreversible vision loss. Ocular neovascularization is also the underlying pathology in sickle cell retinopathy, neovascular glaucoma, retinal vein occlusion and other hypoxic diseases. Recent experimental data show a high correlation between vascular endothelial growth factor expression and retinal neovascularization. (28)

Of numerous angiogenic factors produced from tumor cells, vascular endothelial growth factor (VEGF) is shown to be a major mediator of tumor angiogenesis and neovascularization. Human VEGF monomers exist as five different isoforms, among which $VEGF_{121}$ and $VEGF_{165}$ are most abundant (1, 2). VEGF activities are exerted by its binding to high affinity tyrosine kinase receptors present on endothelial cells lining tumor vasculature. Two such receptors have been isolated: KDR/Flk-1(3, 4) which appears to be the major transducer of VEGF signals and Flt-1(5, 6).

Neuropilin or $VEGF_{165}R$ or the vascular endothelial growth factor receptor, which was originally isolated as a receptor for the collapsin/semaphorin that mediates neuronal cell guidance (7, 8), has been recently cloned as a new isoform specific receptor expressed by endothelial cells for $VEGF_{165}$ (9). The nucleic acid sequence for human neuropilin has been reported (9, 11, 21, 22). Neuropilin acts as a coreceptor for $VEGF_{165}$ binding to KDR/Flk-1 and modulating subsequent bioactivity, i.e. tumor-induced angiogenesis. It is also highly expressed in tumor derived cells such as MDA-MB-231 breast carcinoma cells and PC3 prostate carcinoma cells, among the few tested (9, 10). VEGF has also been shown to bind to Hela, melanoma and NIH 3T3 cells.

Antisense technology has been widely adopted not only as a useful research tool (12), but also as a rational approach to acquire new therapeutic compounds for the treatment of many human diseases including cancer (13, 14). Antisense oligonucleotides can specifically hybridize to mRNA sequences and inhibit expression of proteins that are important in initiation and/or progression of human cancer. Therefore, it would be desirable to identify antisense oligonucleotides directed against neuropilin which act to inhibit the expression and production of neuropilin/$VEGF_{165}R$ with higher specificity and with less toxicity.

SUMMARY OF THE INVENTION

This invention is directed to antisense oligonucleotides which modulate the expression of the neuropilin genes and production of neuropilin/$VEGF_{165}R$ in mammals and pharmaceutical compositions comprising such antisense oligonucleotides. This invention is also related to methods of using such antisense oligonucleotides for inhibiting the proliferation of new capillaries or angiogenesis or neovascularization involved in tumor growth and metastasis in mammals.

Accordingly, in one of its composition aspects, this invention is directed to an antisense oligonucleotide from about 3 to about 100 nucleotides, comprising nucleotides complementary to the neuropilin mRNA of a mammal. The antisense oligonucleotide may be nuclease resistant and may have one or more phosphorothioate internucleotide linkages. The antisense oligonucleotide may further comprise additional nucleotides which are not complementary to the neuropilin mRNA.

In another of its composition aspects, this invention is directed to an antisense oligonucleotide from about 20 to about 100 nucleotides, comprising a sequence selected from the group consisting of SEQ ID NOs: 1–30 set forth in Table 1 which oligonucleotide inhibits neuropilin expression.

In another of its composition aspects, this invention is directed to a vector comprising an oligonucleotide sequence from about 20 to 100 nucleotides comprising a sequence selected from the group consisting of SEQ ID NOs:1–30 as set forth in Table 1 which oligonucleotide inhibits neuropilin expression.

In still another of its composition aspects, this invention is directed to a pharmaceutical composition comprising a pharmaceutically acceptable excipient and an effective amount of an antisense oligonucleotide from about 20 to about 100 nucleotides comprising a sequence selected from the group consisting of SEQ ID NOs: 1–30 as set forth in Table 1 which oligonucleotide inhibits neuropilin expression.

In one of its method aspects, this invention is directed to a method for inhibiting the growth of a mammalian tumor comprising, administering to a mammal suspected of having the tumor an effective amount of an antisense oligonucleotide from about 3 nucleotides to about 100 nucleotides comprising a sequence complementary to mammalian neuropilin mRNA under conditions such that the growth of the tumor is inhibited. The antisense oligonucleotide may be administered with a chemotherapeutic agent.

In another of its method aspects, this invention is directed to a method for inhibiting the metastasis of a mammalian tumor comprising, administering to a mammal suspected of having a metastatic tumor an effective amount of an antisense oligonucleotide from about 3 nucleotides to about 100 nucleotides comprising a sequence complementary to mammalian neuropilin mRNA under conditions such that the metastasis of the tumor is inhibited. The antisense oligonucleotide may be administered with a chemotherapeutic agent.

In another of its method aspects, this invention is directed to a method for inhibiting angiogenesis or neovascularization in a mammal comprising, administering to a mammal an effective amount of an antisense oligonucleotide from about 3 nucleotides to about 100 nucleotides complementary to mammalian neuropilin mRNA under conditions such that neovascularization is inhibitied.

In another of its method aspects, this invention is directed to a method for inhibiting neuropilin expression comprising contacting nucleic acid specific for neuropilin with an antisense oligonucleotide from about 20 nucleotides to about 100 nucleotides comprising a sequence selected from the group consisting of SEQ ID NOs: 1–30 as set forth in Table 1 which oligonucleotide inhibits neuropilin expression.

BRIEF DESCRIPTION OF THE DRAWINGS

FIG. 1A shows the percentage inhibition of the human melanoma cell line C8161; FIG. 1B shows percentage inhibition of the human lung cancer cell line A549; FIG. 1C shows the percentage inhibition of the human melanoma cell line A2058: FIG. 1D shows the percentage inhibition of the human colon cancer cell line HT-29; FIG. 1E shows the percentage inhibition of the human prostate cancer cell line PC-3; and FIG. 1F shows the percentage inhibition of the human pancreatic cancer cell line AsPC-1.

FIG. 5 is the nucleotide sequence of human neuropilin cDNA. [SEQ ID NO:33].

FIG. 6 is the nucleotide sequence of rat neuropilin cDNA. [SEQ ID NO:34].

FIG. 7 is the nucleotide sequence of mouse neuropilin cDNA. [SEQ ID NO:35].

DETAILED DESCRIPTION OF THE INVENTION

Figure 1A:
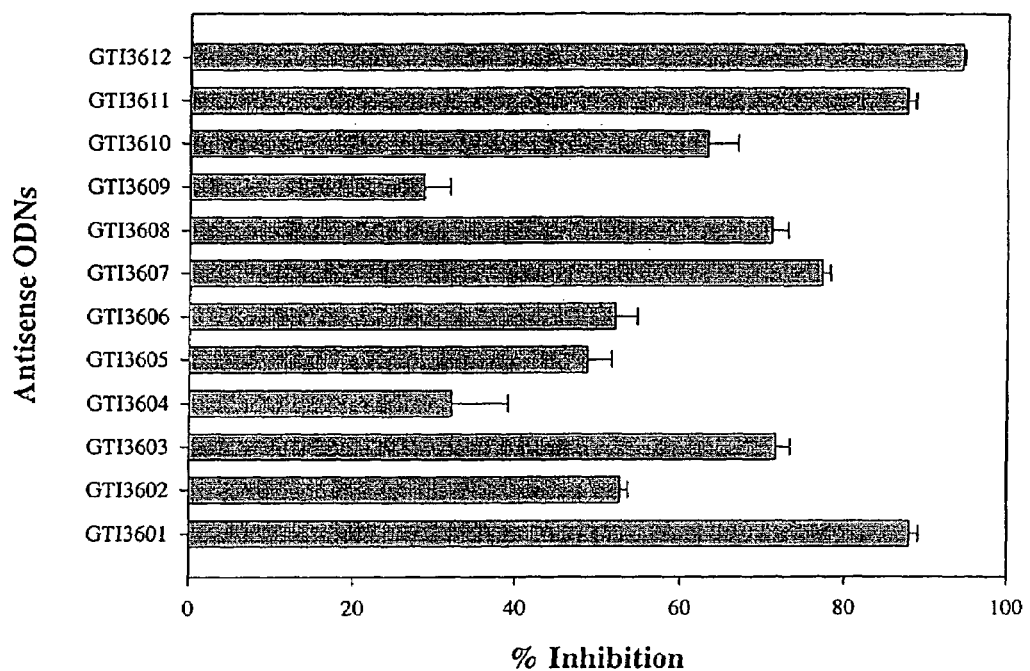
FIGS. 1A–F are graphs of the percentage of inhibition of the colony forming ability of different cell lines by administration of the indicated antisense oligonucleotides.

This invention relates to oligonucleotides complementary to mammalian neuropilin mRNA which oligonucleotide modulate cell growth.

Neuropilin is a receptor for vascular endothelial growth factor or VEGF. VEGF has been found to modulate tumor induced angiogenesis. Neuropilin is also highly expressed in tumor derived cells such a MDA-MB-231 breast carcinoma cells and in tissue culture cells such as Hela and NIH 3T3 cells. This suggests that, in addition to its role in angiogenic stimulation, neuropilin may act, in an autocrine manner, as a sole signal transducer for VEGF activities on tumor cells themselves by enhancing survival, differentiation, or motility. Another possibility may be that neuropilin has storage or sequestration function.

Definitions:

As used herein, the following terms have the following meanings:

The term "antisense oligonucleotide" as used herein means a nucleotide sequence that is complementary to the desired mRNA. Preferably, the antisense oligonucleotide is complementary to that portion of a mammalian neuropilin mRNA or $VEGF_{165}R$ mRNA that effectively acts as a target for inhibiting neuropilin expression. It is contemplated that the antisense oligonucleotide may be complementary to any of the 5' untranslated region of the mRNA, the coding region or the 3' untranslated region of the mRNA. Most preferably, the antisense oligonucleotide is complementary to the nucleotide sequence set forth in FIG. 5.

Without being limited to any theory or mechanism, it is generally believed that the activity of antisense oligonucleotides depends on the binding of the oligonucleotide to the target nucleic acid (e.g. to at least a portion of a genomic region, gene or mRNA transcript thereof), thus disrupting the function of the target, either by hybridization arrest or by destruction of target RNA by RNase H (the ability to activate RNase H when hybridized to RNA) resulting in inhibition of neuropilin expression.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligomers may be preferred over naturally occurring forms because of the properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells) or two or more oligonucleotides of the invention may be joined to form a chimeric oligonucleotide.

The antisense oligonucleotides of the present invention may be ribonucleic or deoxyribonucleic acids and may contain naturally occurring or synthetic monomeric bases, including adenine, guanine, cytosine, thymine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines or guanines, 5-trifluoromethyl uracil and 5-trifluoro cytosine. The modifications may also include attachment of other chemical groups such as methyl, ethyl, propyl groups to the various parts of the oligonucleotides including the sugar, base or backbone components.

The antisense oligonucleotides of the invention may also comprise modified phosphorus oxygen heteroatoms in the phosphate backbone, short chain alkyl or cycloalkyl intersugar linkages or short chain heteroatom or heterocyclic intersugar linkages. For example, the antisense oligonucleotides may contain methyl phosphonates, phosphorothioates, phosphorodithioates, phosphotriesters, and morpholino oligomers. The antisense oligonucleotides may comprise phosphorothioate bonds linking between the four to six 3'-terminus nucleotides. The phosphorothioate bonds may link all the nucleotides. The phosphorothioate linkages may be mixed $R_P$ and $S_P$ enantiomers, or they may be stereoregular or substantially stereoregular in either $R_P$ or $S_P$ form.

The antisense oligonucleotides may also have sugar minetics. The oligonucleotide may have at least one nucleotide with a modified base and/or sugar, such as a 2'-O-substituted ribonucleotide. For purposes of the invention, the term 2'-O-substituted" means substitution of the 2' position of the pentose moiety with an —O— lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups. The oligonucleotides of the invention may include four or five ribonucleotides 2'-O-alkylated at their 5' terminus and/or four or five ribonucleotides 2'-O-alkylated at their 3' terminus.

The antisense oligonucleotides of the invention may also comprise nucleotide analogues wherein the structure of the nucleotide is fundamentally altered. An example of such an oligonucleotide analogue is a peptide nucleic acid (PNA) wherein the deoxyribose (or ribose) phosphate backbone in DNA (or RNA) is replaced with a polyamide backbone which is similar to that found in peptides (Nielsen et al.[29]; Good and Nielsen[30]; Buchardt, deceased, et al.[31], U.S. Pat. No. 5,766,855; Buchardt, deceased, et al.⁼, U.S. Pat. No. 5,719,262). PNA analogues have been shown to be resistant to degradation by enzymes and to have extended lives in vivo and in vitro. PNAs also bind more strongly to a complementary DNA sequence than to a naturally occurring nucleic acid molecule due to the lack of charge repulsion between the PNA strand and the DNA strand.

The oligonucleotides of the present invention may also include other nucleotides comprising polymer backbones, cyclic backbones, or acyclic backbones. For example, the nucleotides may comprise morpholino backbone structures (U.S. Pat. No. 5,034,5063[33]).

The oligonucleotides of the present invention are "nuclease resistant" when they have either been modified such that they are not susceptible to degradation by DNA and RNA nucleases or alternatively they have been placed in a delivery vehicle which in itself protects the oligonucleotide from DNA or RNA nucleases. Nuclease resistant oligonucleotides include, for example, methyl phosphonates, phosphorothioates, phosphorodithioates, phosphotriesters, and morpholino oligomers. Suitable delivery vehicles for conferring nuclease resistance include, for example liposomes.

The oligonucleotides of the present invention may also contain groups, such as groups for improving the pharmacokinetic properties of an oligonucleotides, or groups for improving the pharmacodynamic properties of an oligonucleotide.

The antisense oligonucleotides are selected from the sequence complementary to the neuropilin gene. Preferably, the sequence exhibits the least likelihood of showing duplex formation, hair-pin formation, and homooligomer/sequence repeats but has a high to moderate potential to bind to the neuropilin gene sequences. These properties may be determined using the computer modeling program OLIGO Primer Analysis Software, Version 5.0 (distributed by National Biosciences, Inc., Plymouth, Minn.). This computer program allows the determination of a qualitative estimation of these five parameters.

Alternatively, the antisense oligonucleotides may also be selected on the basis that the sequence is highly conserved for the neuropilin gene between two or more mammalian species. These properties may be determined using the BLASTN program (Altschul, et al.[34]) of the University of Wisconsin Computer group (GCG) software (Devereux J. et al.[35]) with the National Center for Biotechnology Information (NCBI) databases.

The antisense oligonucleotides may include mutations, such as substitutions, insertions and deletions. Preferably there will be less that 10% of the sequence having mutations.

The antisense oligonucleotides generally comprise from at least about 3 nucleotides or nucleotide analogs, more preferably they are at least about 5 nucleotides, more preferably they are at least about 7 nucleotides, more preferably they are at least about 9 nucleotides and most preferably they are at least about 20 nucleotides. The antisense oligonucleotides are preferably less than about 100 nucleotides or nucleotide analogs, more preferably, less than about 50 nucleotides or nucleotide analogs, most preferably less than about 35 nucleotide or nucleotide analogs.

Preferably, the antisense oligonucleotides comprise the sequences set forth in Table 1 (below).

TABLE 1

Antisense oligonucleotides having a sequence complementary to the human neuropilin mRNA

| SEQ ID NO. | Name | Sequence 5'-3' | Tm (° C.) | ΔG (kcal/mol) |
|---|---|---|---|---|
| 1 | GTI3601 | GAG CGG CAG CCC CCT CTC CA | 74.6 | −46.5 |
| 2 | GTI3602 | CGA GCA CGG CGC AGA GGA GC | 74.2 | −45.7 |
| 3 | GTI3603 | GGA CGA GGG CGA GCA CGG CG | 78.0 | −48.6 |
| 4 | GTI3604 | TGG GTC CGG AGC CTG AAT CA | 69.0 | −42.2 |
| 5 | GTI3605 | TTT TTC AGG GAA TCC GGG GG | 69.1 | −44.6 |
| 6 | GTI3606 | GGG TAG TTC AGG CGG GAG CG | 69.9 | −44.3 |
| 7 | GTI3607 | AAT GGC GCC CTG TGT CCC GA | 73.4 | −45.4 |
| 8 | GTI3608 | GTG CCC AGC CAG AGC GAC TG | 69.5 | −42.0 |
| 9 | GTI3609 | TGA GGT GCG GGT GGA AGT GC | 69.6 | −42.0 |
| 10 | GTI3610 | GTG CCG ACG TGG GAC CCA GA | 71.6 | −43.1 |
| 11 | GTI3611 | GAC CCC CAG GGC ACT CAT GG | 70.1 | −42.9 |
| 12 | GTI3612 | CGA CCC CAC AGA CAG CCC CC | 72.4 | −44.4 |
| 13 | GTI3613 | TCT CTG TCC TCC AAA TCG AA | 58.6 | −36.5 |
| 14 | GTI3614 | TGC TTC CCA CCC TGA ATG AT | 63.3 | −39.2 |
| 15 | GTI3615 | TGG GAA TAG ATG AAG TTG CC | 58.4 | −37.1 |
| 16 | GTI3617 | TCC TCT GGC TTC TGG TAG CG | 63.8 | −39.9 |
| 17 | GTI3618 | AGG TTT CCT TTT CCG ATT TC | 59.0 | −38.6 |
| 18 | GTI3619 | GTG CTC CCT GTT TCA TCA AT | 58.0 | −36.2 |
| 19 | GTI3620 | CAT TGC CTG GCT TCC TGG AG | 66.2 | −41.1 |
| 20 | GTI3621 | CCC AGG GCA CTC ATG GCT AT | 65.5 | −41.0 |
| 21 | GTI3622 | GCT GAG AAA CCT TCT TTT GC | 57.9 | −37.0 |
| 22 | GTI3623 | AAC ATC TGT GGG GTT GGT GT | 60.3 | −36.9 |
| 23 | GTI3624 | TCG GAC AAA TCG AGT TAT CA | 57.1 | −36.0 |
| 24 | GTI3625 | CAA CAT TCC AGA GCA AGG AT | 58.2 | −36.5 |
| 25 | GTI3626 | CGA TCT TGA ACT TCC TCA TG | 56.0 | −35.2 |
| 26 | GTI3627 | CCT GTG AGC TGG AAG TCA TC | 58.2 | −35.7 |
| 27 | GTI3628 | CAT GTG ATA CCA GAA GGT CA | 53.9 | −33.5 |
| 28 | GTI3629 | CCA ACA GGC ACA GTA CAG CA | 60.8 | −36.7 |
| 29 | GTI3630 | ACC ATC CAC AAG TTC AAA GT | 54.8 | −34.5 |
| 30 | GTI3631 | ACC ACA GGG CTC ACC AGG CG | 71.0 | −43.2 |

The antisense oligonucleotides of Table I were selected from the sequence complementary to the human Neuropilin/

VEGF$_{165}$R mRNA such that the sequence exhibits the least likelihood of showing duplex formation, hairpin formation, and homooligomers/sequence repeats but has a high potential to bind to the Neuropilin/VEGF$_{165}$R mRNA sequence. In addition, false priming to other frequently occurring or repetitive sequences in human and mouse was eliminated. These properties were determined using the computer modeling program OLIGO® Primer Analysis Software, Version 5.0 (distributed by National Biosciences, Inc., Plymouth, Minn.).

In Table 1 the "Tm" is the melting temperature of an oligonucleotide duplex calculated according to the nearest-neighbour thermodynamic values. At this temperature 50% of nucleic acid molecules are in duplex and 50% are denatured. The "ΔG" is the free energy of the oligonucleotide, which is a measurement of an oligonucleotide duplex stability.

The term "alkyl" refers to monovalent alkyl groups preferably having from 1 to 20 carbon atoms and more preferably 1 to 6 carbon atoms. This term is exemplified by groups such as methyl, ethyl, n-propyl, iso-propyl, n-butyl, iso-butyl, n-hexyl, and the like.

The term "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like.

The term "halo" or "halogen" refers to fluoro, chloro, bromo and iodo and preferably is either fluoro or chloro.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "pharmaceutically acceptable" means a non-toxic material that does not interfere with the effectiveness of the biological activity of the active ingredient(s). The material is compatible with a biological system such as a cell, cell culture, tissue or organism.

The term "pharmaceutically acceptable salt" refers to salts which retain the biological effectiveness and properties of the antisense oligonucleotides of this invention and which are not biologically or otherwise undesirable. In many cases, the antisense oligonucleotides of this invention are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl)amines, alkenyl amines, dialkenyl amines, trialkenyl amines, substituted alkenyl amines, di(substituted alkenyl)amines, tri(substituted alkenyl) amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethylamine, diethylamine, tri(isopropyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "neuropilin gene" refers to any gene which encodes a protein that is capable of acting as a receptor for semaphorin or VEGF. Preferably, the neuropilin mRNA has a sequence substantially similar to that shown in FIGS. 5, 6 or 7.

The term "complementary to" means that the antisense oligonucleotide sequence is capable of binding to the target sequence, i.e. the neuropilin gene (or mRNA). Preferably, the antisense oligonucleotide binds to the nucleic acid sequence under physiological conditions, e.g. by Watson-Crick base pairing (interaction between oligonucleotide and single-stranded nucleic acid) or by Hoogsteen base pairing (interaction between oligonucleotide and double-stranded nucleic acid) or by any other means including in the case of an oligonucleotide binding to RNA, causing pseudoknot formation. Binding by Watson-Crick or Hoogsteen base pairing under physiological conditions is measured as a practical matter by observing interference with the function of the nucleic acid sequence.

Preferably the antisense oligonucleotide sequence has at least about 75% identity with the target sequence, preferably at least about 90% identity and most preferably at least about 95% identity with the target sequence allowing for gaps or mismatches of several bases. Identity can be determined, for example, by using the BLASTN program of the University of Wisconsin Computer Group (GCG) software. Preferably the antisense oligonucleotide sequence hybridizes to the neuropilin mRNA with a melting temperature of at least 45° C., more preferably at least about 50° C. and most preferably at least about 55° C. as determined by the OLIGO primer analysis software program version 5.0 described herein.

The term "inhibiting growth" means a reduction or inhibition in the growth of at least one tumor cell type by at least 10%, more preferably of at least 50% and most preferably of at least 75%. The reduction in growth can be determined for tumor cells by measuring the size of the tumor in nude mice or the inability of the tumor cells to form colonies in vitro.

The term "inhibiting angiogenesis" means a reduction or inhibition in neovascularization. This can be determined by methods known in the art. A murine model of oxygen-induced retinal neovascularization has been established which occurs in 100% of treated animals and is quantifiable (45, 46). Using this model, a correlation between the inhibition of neuropilin and inhibition of retinal neovascularization could be measured. This result may also be confirmed by changes in expression level of neuropilin by Northern blot and in situ hybridization analysis.

The term "inhibiting metastasis" means reducing or inhibiting the number of metastatic tumors that develop, preferably by at least 10%, more preferably by at least 50%. This can be determined by the methods set forth in the Examples and other methods known in the art.

The term "inhibiting expression of neuropilin" means that the antisense oligonucleotide reduces the level of neuropilin mRNA or the level of neuropilin protein produced by the cell when the oligonucleotide is administered to the cell.

The term "mammal" or "mammalian" means all mammals including humans, ovines, bovines, equines, swine, canines, felines and mice, etc., preferably it means humans.

A "mammal suspected of having a tumor" means that the mammal may have a proliferative disorder or tumor or has been diagnosed with a proliferative disorder or tumor or has been previously diagnosed with a proliferative disorder or tumor, the tumor has been surgically removed and the mammal is suspected of harboring some residual tumor cells.

Preparation of the Antisense Oligonucleotides

The antisense oligonucleotides of the present invention may be prepared by conventional and well-known techniques. For example, the oligonucleotides may be prepared using solid-phase synthesis and in particular using commercially available equipment such as the equipment available from Applied Biosystems Canada Inc., Mississauga, Canada. The oligonucleotides may also be prepared by enzymatic digestion of the naturally occurring neuropilin gene by methods known in the art.

These oligonucleotides can be prepared by the art recognized methods such as phosphoramidate or H-phosphoate chemistry which can be carried out manually or by an automated synthesizer as described by Uhlmann et al.(43) and Agrawal et al.(44)

Isolation and Purification of the Antisense Oligonucleotides

Isolation and purification of the antisense oligonucleotides described herein can be effected, if desired, by any suitable separation or purification such as, for example, filtration, extraction, crystallization, column chromatography, thin-layer chromatography, thick-layer chromatography, preparative low or high-pressure liquid chromatography or a combination of these procedures. However, other equivalent separation or isolation procedures could, of course, also be used.

An expression vector comprising the antisense oligonucleotide sequence may be constructed having regard to the sequence of the oligonucleotide and using procedures known in the art.

Vectors can be constructed by those skilled in the art to contain all the expression elements required to achieve the desired transcription of the antisense oligonucleotide sequences. Therefore, the invention provides vectors comprising a transcription control sequence operatively linked to a sequence which encodes an antisense oligonucleotide. Suitable transcription and translation elements may be derived from a variety of sources, including bacterial, fungal, viral, mammalian or insect genes. Selection of appropriate elements is dependent on the host cell chosen.

Reporter genes may be included in the vector. Suitable reporter genes include β-galactosidase (e.g. lacZ), chloramphenicol, acetyl-transferase, firefly luciferase, or an immunoglobulin or portion thereof. Transcription of the antisense oligonucleotide may be monitored by monitoring for the expression of the reporter gene.

The vectors can be introduced into cells or tissues by any one of a variety of known methods within the art. Such methods can be found generally described in Sambrook et al.[24]; Ausubel et al.[25]; Chang et al.[36]; Vega et al.[37]; and Vectors: A Survey of Molecular Cloning Vectors and Their Use[38] and include, for example, stable or transient transfection, lipofection, electroporation and infection with recombinant viral vectors.

Introduction of nucleic acids by infection offers several advantages. Higher efficiency and specificity for tissue type can be obtained. Viruses typically infect and propagate in specific cell types. Thus, the virus' specificity may be used to target the vector to specific cell types in vivo or within a tissue or mixed culture of cells. Viral vectors can also be modified with specific receptors or ligands to alter target specificity through receptor mediated events.

It is contemplated that the oligonucleotide of this invention may be a ribozyme which cleaves the mRNA. The ribozyme preferably has a sequence homologous to a sequence of an oligonucleotide of the invention and the necessary catalytic center for cleaving the mRNA. For example, a homologous ribozyme sequence may be selected which destroys the neuropilin mRNA. The ribozyme type utilized in the present invention may be selected from types known in the art. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan 1994, U.S. Pat. No. 5,225,347[39]). Hammerhead and hairpin ribozyme motifs are most commonly adapted for trans cleavage of mRNAs for gene therapy (Sullivan 1994). Hairpin ribozymes are preferably used in the present invention. In general, the ribozyme is from 30 to 100 nucleotides in length.

The oligonucleotides of the invention may be insolubilized. For example, the oligonucleotide may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinylether-maleic acid copolymer, amino acid copolymer, ethylene-maleic acid copolymer, nylon, silk etc. The carrier may in the shape of, for example, a tube, test plate, beads disc, sphere etc.

The insolubilized oligonucleotide may be prepared by reacting the material with the suitable insoluble carrier using known chemical or physical methods, for example, cyanogen bromide coupling.

Pharmaceutical Formulations

When employed as pharmaceuticals, the antisense oligonucleotides are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. The pharmaceutical composition is, for example, administered intravenously. It is contemplated that the pharmaceutical composition may be administered directly into the tumor to be treated.

This invention also includes pharmaceutical compositions which contain, as the active ingredient, one or more of the antisense oligonucleotides associated with pharmaceutically acceptable carriers or excipients. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 1% to about 95%, more usually about 5% to about 90% of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The antisense oligonucleotide is effective over a wide dosage range and is generally administered in a pharmaceutically effective amount. An effective amount is that amount which when administered alleviates the symptoms. Preferably the effective amount is that amount able to inhibit tumor cell growth. Preferably the effective amount is from about 0.1 mg/kg body weight to about 20 mg/kg body weight. It will be understood, however, that the amount of the antisense oligonucleotide actually administered will be determined by a physician, in the light of the relevant circumstances, including the condition to be treated, the chosen route of administration, the actual compound administered, the age, weight, and response of the individual patient, the severity of the patient's symptoms, and the like. The course of therapy may last from several days to several months or until diminution of the disease is achieved. The antisense oligonucleotide may be administered in combination with other known therapies. When co-administered with one or more other therapies, the oligonucleotide may be administered either simultaneously with the other treatments(s), or sequentially. If administered sequentially, the attending physician will decide on the appropriate sequence of administering the oligonucleotide in combination with the other therapy.

For preparing solid compositions such as tablets, the principal active ingredient/antisense oligonucleotide is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The pharmaceutical composition of the invention may be in the form of a liposome, in which the oligonucleotide is combined, in addition to other pharmacuetically acceptable carriers, with amphipathic agents such as lipids which exist in aggregated form as micells, insoluble monolayers, liquid crystals or lamellar layers which are in aqueous solution. Suitable lipids for liposomal formulation include, without limitation, monoglycerides, diglycerides, sulfatides, lysolecithin, phospholipids, saponin, bile acids and the like. One particularly useful lipid carrier is lipofectin. Preparation of such liposomal formulations is within the skill in the art, for example, International Patent No. WO97/21808 (28) The pharmaceutical composition may further include compounds such as cyclodextrins and the like which enhance delivery of oligonucleotides into cells or slow release polymers.

Another preferred formulation employed in the methods of the present invention employs transdermal delivery devices ("patches"). Such transdermal patches may be used to provide continuous or discontinuous infusion of the antisense oligonucleotides of the present invention in controlled amounts. The construction and use of transdermal patches for the delivery of pharmaceutical agents is well known in the art. See, for example, U.S. Pat. No. 5,023,252[40], herein incorporated by reference. Such patches may be constructed for continuous, pulsatile, or on demand delivery of pharmaceutical agents.

Another preferred method of delivery involves "shotgun" delivery of the naked antisense oligonucleotides across the dermal layer. The delivery of "naked" antisense oligonucleotides is well known in the art. See, for example, Felgner et al., U.S. Pat. No. 5,580,859[41]. It is contemplated that the antisense oligonucleotides may be packaged in a lipid vesicle before "shotgun" delivery of the antisense oligonucleotide.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A formulation may be prepared as follows:

| Ingredient | Quantity |
| --- | --- |
| Active Ingredient | 5.0 mg |
| Corn Oil | 1.0 mL |

FORMULATION EXAMPLE 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Other suitable formulations for use in the present invention can be found in *Remington's Pharmaceutical Sciences*[23].

The antisense oligonucleotides or the pharmaceutical composition comprising the antisense oligonucleotides may be packaged into convenient kits providing the necessary materials packaged into suitable containers.

The antisense oligonucleotides of the invention in the form of a therapeutic formulation are useful in treating diseases, and disorders and conditions associated with angiogenesis and neovascularization including, but not limited to, retinal neovascularization and tumor growth. In such methods a therapeutic amount of a oligonucleotide effective in inhibiting the expression of neuropilin is administered to a cell. This cell may be part of a cell culture, a tissue culture, or the whole body of a mammal such as a human.

The oligonucleotides and ribozymes of the invention modulate tumor cell growth. Therefore methods are provided for interfering or inhibiting tumor cell growth in a mammal comprising contacting the tumor or tumor cells with an antisense oligonucleotide of the present invention. Without being limited to a theory or mechanism, it is believed that the antisense oligonucleotides may inhibit tumor growth in two ways. They may inhibit growth in an autocrine manner by acting directly on the tumor cells. Alternatively or additionally, the antisense oligonucleotides may act by inhibiting neovascularization associated with tumor growth, thereby reducing the blood supply available to the tumor.

The term "contact" refers to the addition of an oligonucleotide, ribozyme, etc. to a cell suspension or tissue sample or administering the oligonucleotides etc. directly or indirectly to cells or tissues within an animal.

The methods may be used to treat proliferative disorders including various forms of cancer or tumors such as sarcomas, melanomas, adenomas, carcinomas of solid tissue, hypoxic tumors, squamous cell carcinomas of the mouth, throat, larynx and lung, genitourinary cancers such as cervical and bladder cancer, hematopoietic cancers, colon cancer, breast cancer, pancreatic cancer, renal cancer, brain cancer, skin cancer, liver cancer, head and neck cancers, and nervous system cancers, as well as benign lesions such as papillomas.

The methods may be use to treat neovascular disorders such as diabetic retinopathy, retinopathy of prematurity and age related macular degeneration.

The oligonucleotides of the invention may also be used to treat drug resistant tumors. Examples of drug resistant tumors are tumors resistant to such chemotherapeutic agents as 5-fluorouracil, mitomycin C, methotrexate or hydroxyurea and tumors expressing high levels of P-glycoprotein which is known to confer resistance to multiple anticancer drugs such as colchicine, vinblastine and doxorubicin; or tumors expressing multi-drug resistance protein as described by Dreeley et al.[42]. Accordingly, it is contemplated that the oligonucleotides of the present invention may be administered in conjunction with or in addition to known anticancer compounds or chemotherapeutic agents. Chemotherapeutic agents are compounds which may inhibit the growth of tumors. Such agents, include, but are not limited to, 5-fluorouracil, mitomycin C, methotrexate and hydroxyurea. It is contemplated that the amount of chemotherapeutic agent administered may be either an effective amount, i.e. an amount sufficient to inhibit tumor growth or a less than effective amount.

The oligonucleotides of the present invention have been found to reduce the growth of tumors that are metastatic such as MDA-MB-231 breast adenocarcinoma, HT-29 colon adenocarcinoma, A549 lung carcinoma, and A2058 melanoma cancer cells. In an embodiment of the invention, a method is provided for reducing the growth of metastastic tumors in a mammal comprising administering an amount of an oligonucleotide complementary to the neuropilin mRNA, or an oligonucleotide shown in Table 1.

The oligonucleotides of the present invention may reduce angiogenesis. In one embodiment of the invention a method is provided for the treatment of neovascular disorders.

The oligonucleotides may be delivered using viral or non-viral vectors. Sequences may be incorporated into cassettes or constructs such that an oligonucleotide of the invention is expressed in a cell. Preferably, the construct contains the proper transcriptional control region to allow the oligonucleotide to be transcribed in the cell.

Therefore, the invention provides vectors comprising a transcription control sequence operatively linked to a sequence which encodes an oligonucleotide of the invention. The present invention further provides host cells, selected from suitable eucaryotic and procaryotic cells, which are transformed with these vectors.

Suitable vectors are known and preferably contain all of the expression elements necessary to achieve the desired transcription of the sequences. Phagemids are a specific example of such beneficial vectors because they can be used either as plasmids or as bacteriophage vectors. Examples of the vectors include viruses such as bacteriophages, baculoviruses, retroviruses, DNA viruses, liposomes and other recombination vectors. The vectors can also contain elements for use in either procaryotic or eucaryotic host systems. One of ordinary skill in the art will know which host systems are compatible with a particular vector.

The vectors can be introduced into the cells by stable or transient transfection, lipofection, electroporation and infection with recombinant viral vectors.

Additional features can be added to the vector to ensure its safety and/or enhance its therapeutic efficacy. Such features include, for example, markers that can be used to negatively select against cells infected with recombinant viruses. An example of such a negative selection marker is the TK gene which confers sensitivity to the antiviral gancyclovir. Features that limit expression to particular cell types can also be included. Such features include, for example, promoter and regulatory elements that are specific for the desired cell type.

Retroviral vectors are another example of vectors useful for the in vivo introduction of a desired nucleic acid because they offer advantages such as lateral infection and targeting specificity. Lateral infection is the process by which a single infected cell produces many progeny virions that infect neighboring cells. The result is that a large area becomes rapidly infected.

A vector to be used in the methods of the invention may be selected depending on the desired cell type to be targeted. For example, if breast cancer is to be treated, then a vector specific for epithelial cells may be used. Similarly, if cells of the hematopoietic system are to be treated, then a viral vector that is specific for blood cells is preferred.

Utility

The antisense oligonucleotides of the present invention may be used for a variety of purposes. They may be used to inhibit the expression of the neuropilin gene in a mammalian cell, resulting in the inhibition of growth of that cell. They may be used to inhibit tumor cell growth and/or neovascularization. The oligonucleotides may be used as hybridization probes to detect the presence of the neuropilin mRNA in mammalian cells. When so used the oligonucleotides may be labeled with a suitable detectable group (such as a radioisotope, a ligand, another member of a specific binding pair, for example, biotin). Finally, the oligonucleotides may be used as molecular weight markers.

In order to further illustrate the present invention and advantages thereof, the following specific examples are given but are not meant to limit the scope of the claims in any way.

EXAMPLES

In the examples below, all temperatures are in degrees Celsius (unless otherwise indicated) and all percentages are weight percentages (also unless otherwise indicated).

In the examples below, the following abbreviations have the following meanings. If an abbreviation is not defined, it has its generally accepted meaning:

| | |
|---|---|
| AS = | antisense |
| cDNA = | complementary deoxyribonucleic acid |
| ODN = | oligonucleotide |
| μM = | micromolar |
| mM = | millimolar |
| M = | molar |
| ml = | milliliter |
| μl = | microliter |
| mg = | milligram |
| μg = | microgram |
| PAGE = | polyacrylamide gel electrophoresis |
| rpm = | revolutions per minute |
| ΔG = | free energy, a measurement of oligonucleotide duplex stability |
| kcal = | kilocalories |
| FBS = | fetal bovine serum |
| DTT = | dithiothrietol |

-continued

| | |
|---|---|
| SDS = | sodium dodecyl sulfate |
| PBS = | phosphate buffered saline |
| PMSF = | phenylmethylsulfonyl fluoride |
| GAPDH = | glyceraldehyde-3-phosphate dehydrogenase |
| IgG = | immunoglobulin G |
| kDa = | kilodalton |
| PCR = | polymerase chain reaction |
| Tris-Hcl = | Tris(hydroxymethyl)aminomethane-hydrochloric acid |
| TRIzol = | total RNA isolation reagent |
| VEGF = | vascular endothelial growth factor |

General Methods in Molecular Biology:

Standard molecular biology techniques known in the art and not specifically described were generally followed as in Sambrook et al.[24]; Ausubel et al.[25]; and Perbal[26].

Oligonucleotides

The antisense oligonucleotides were selected from the sequence complementary to the neuropilin mRNA such that the sequence exhibits the least likelihood of showing duplex formation, hairpin formation, and homooligomers/sequence repeats but has a high potential to bind to the neuropilin mRNA sequence. In addition, a false priming to other frequently occurring or repetitive sequences in human and mouse was eliminated. These properties were determined using the computer modeling program OLIGO® Primer Analysis Software, Version 5.0 International Biosciences, Inc. Plymouth Minn.). Based on this analysis, phosphorothioate antisense oligonucleotides were designed and then made by methods well known in the art.

Cell Lines

Seven different human cancer cell lines including lung carcinoma (A549), melanoma (C8161), breast cell adenocarcinoma (MDA-MB-231), metastatic pancreatic adenocarcinoma (AsPC-1), colon adenocarcinoma (HT-29), human melanoma cell line A2058, human prostate cancer PC3 were obtained from American Type Culture Collection (ATCC). The cell lines were maintained in α-MEM medium (Gibco BRL, Gaithersburg, Md.) supplemented with 10% fetal bovine serum (FBS).

Example 1

The Inhibition of Growth of Cancer Cell Lines by Antisense Oligonucleotides Complementary to Neuropilin The colony forming ability of cancer cell lines treated with different antisense oligonucleotides was estimated using a method previously described (Choy et al.[18]). Specifically, aliquots of a tumor cell suspension were seeded into 60 mm tissue culture dishes at a density of approximately $1 \times 10^4$ and incubated overnight at 37° C. in α-MEM medium supplemented with 10% FBS. Cells were washed once in 5 ml of PBS and treated with 0.2 μM of the indicated antisense oligonucleotides in the presence of cationic lipid (Lipofectin reagent, final concentration, 5 μg/ml, Gibco-BRL, Gaithersburg, Md.) for 4 hours. The antisense oligonucleotides were removed by washing the cells once with PBS and the cells were cultured in growth medium (α-MEM medium supplemented with 10% FBS) for 7 to 10 days at 37° C. Colonies were stained with methylene blue and scored by direct counting as described (Choy et al.[18] and Huang and Wright[20]). Percent inhibition was calculated by comparison with the number of colonies present in cultures grown in the absence of antisense oligonucleotides. All experiments were performed in quadruplicate.

Figure 1B:
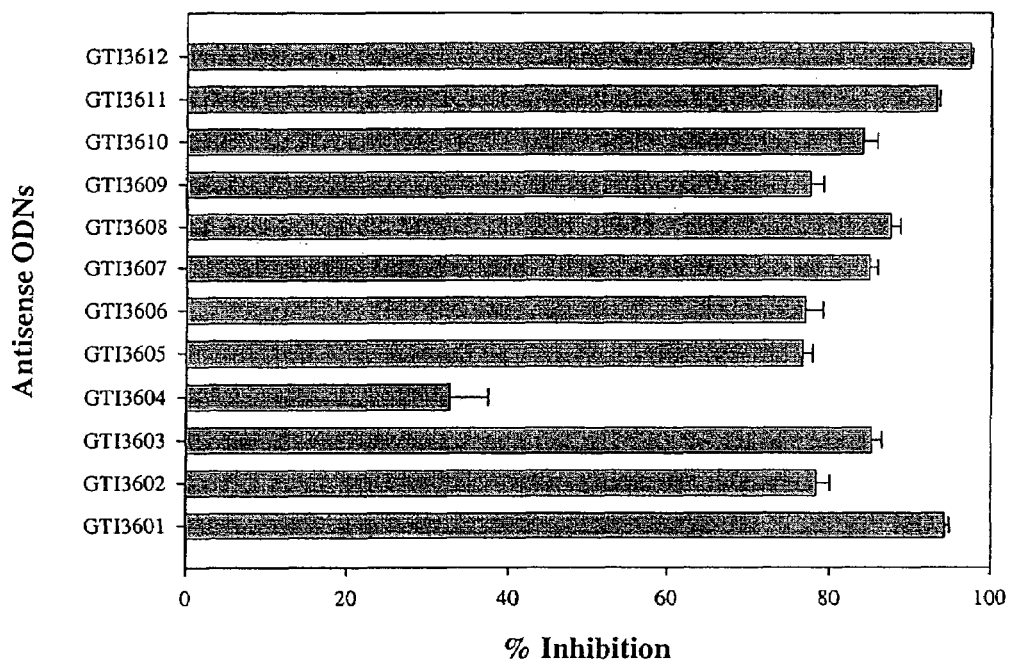
Figure 1C:
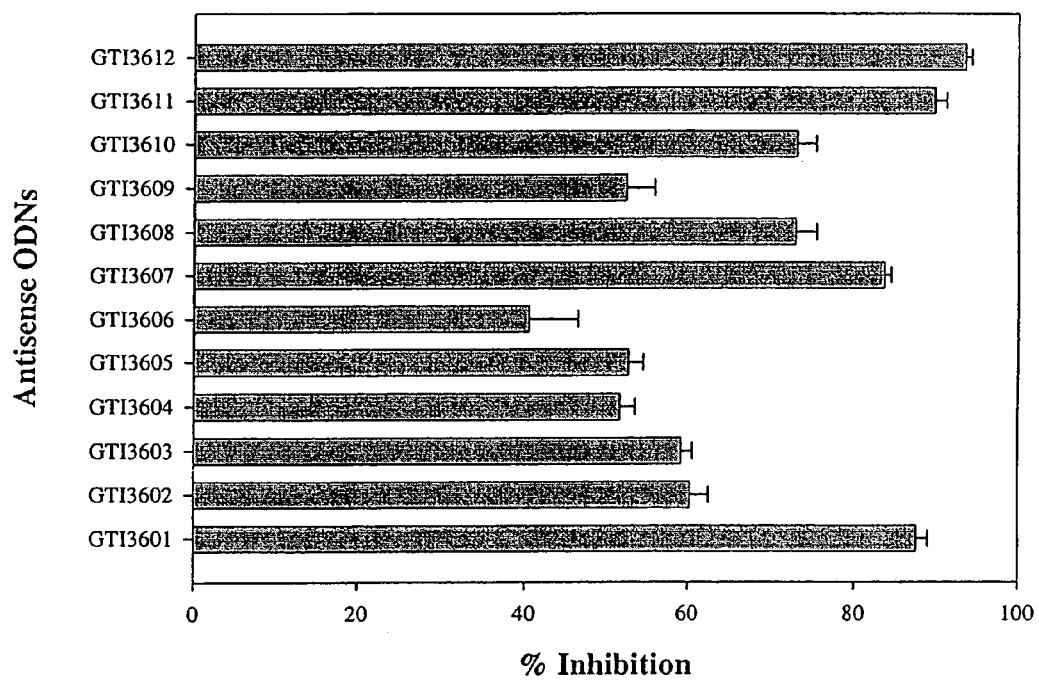
Figure 1D:
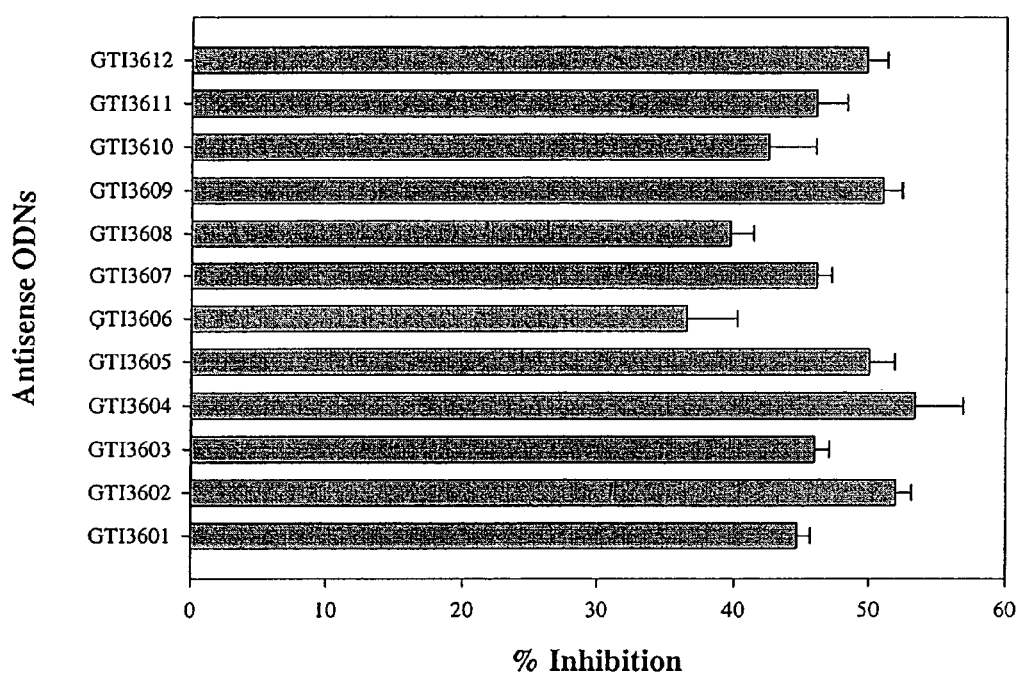
Figure 1E:
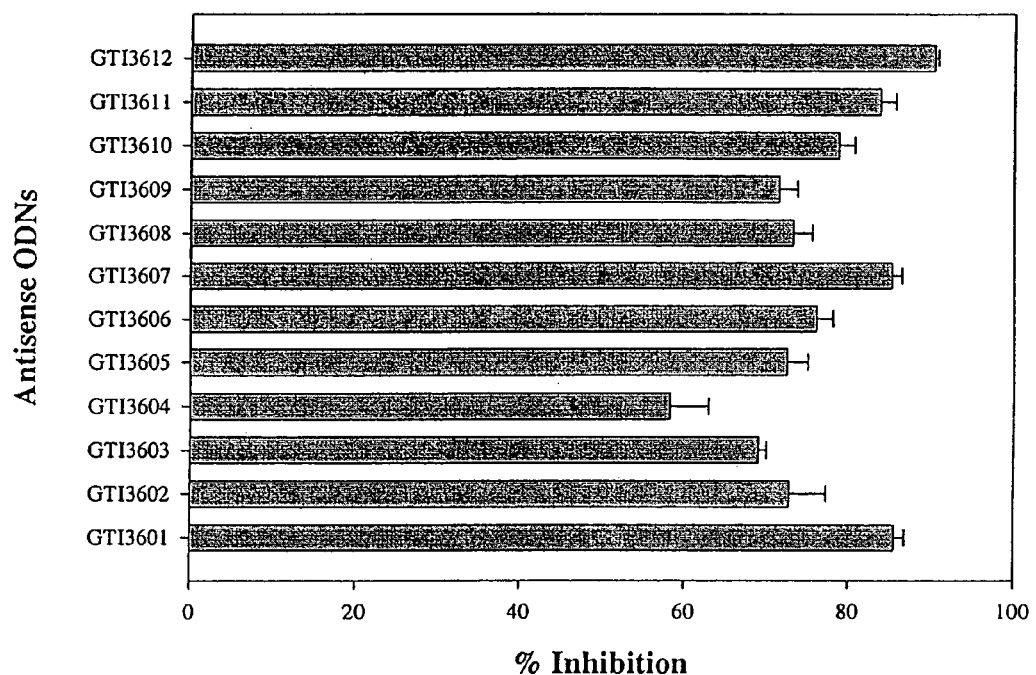
Figure 1F:
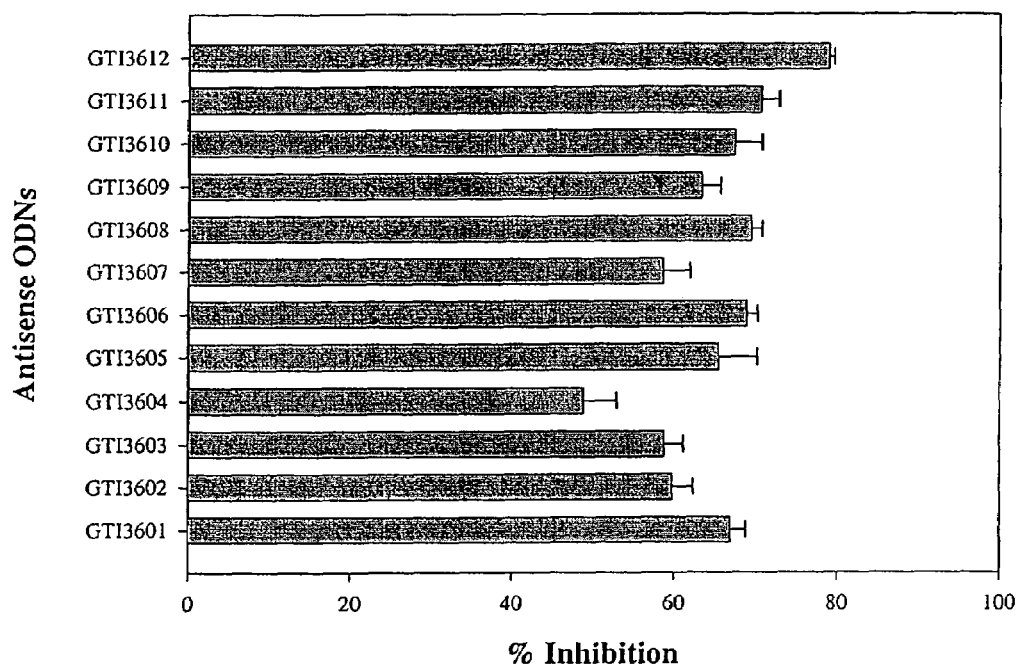

The antisense oligonucleotides exerted inhibitory effects on the colony forming ability of the human tumor cell lines. The percent inhibition of each antisense oligonucleotide is shown in FIG. 1A for human melanoma cell line C8161; FIG. 1B for human lung cancer cell line A549; FIG. 1C for human melanoma cell line A2058: FIG. 1D for human colon cancer cell line HT-29; FIG. 1E for human prostate cancer cell line PC-3; and FIG. 1F for human pancreatic cancer cell line AsPC-1.

Example 2

Decreased mRNA Levels Following Treatment with Antisense Oligonucleotides Complementary to Neuropilin Human melanoma cancer cells (A2058) or breast cancer cells (MDA-MB-231) were grown to subconfluency (70–80%) and were treated with 0.2 μM of phosphorothioate antisense oligonucleotides complementary to neuropilin for 4 hours in the presence of cationic lipid (Lipofectin reagent, final concentration, 5 μg/ml, Gibco-BRL) and Opti-MEM (Gibco-BRL). Cells were washed once with PBS and incubated for 16 hours in α-MEM medium (Gibco-BRL) containing 10% FBS. Total RNA was prepared in TRIzol reagent (Gibco-BRL) and Northern blot analysis was performed as described in Hurta and Wright(27) with some modifications. The bolts were hybridized with $^{32}$P-labeled 598 bp PCR fragments synthesized using forward primer (5'-CGC TCC CGC CTG AAC TAC CC-3') [SEQ ID NO:31], reverse primier (5'-TCC CAC CCT GAA TGA TGA TG-3') [SEQ ID NO:32] and the human colorectal adenocarcinoma 5'-stretch plus cDNA library (Clonetech, Palo Alto Calif.) as a template. Human neuropilin/VEGF$_{165}$R mRNA was expressed as a ~7 kb nucleotide transcript (Soker et al.[9]). Equal RNA loading was demonstrated by methylene blue staining of the blot prior to hybridization.

Figure 2A:
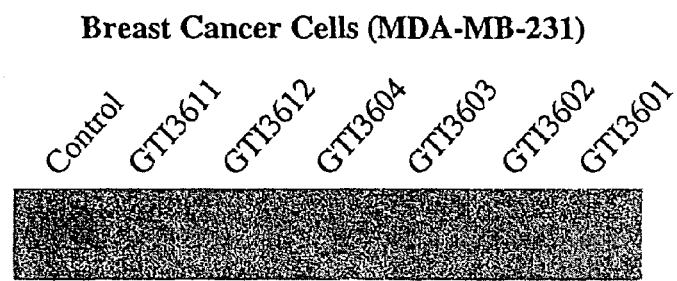
FIGS. 2A and 2B are autoradiographs of Northern Blots of RNA from either human melanoma cancer cell line A2058 (FIG. 2B) or human breast cancer cell line MDA-MB-231 (FIG. 2A) after administration with one of the following antisense oligonucleotides: GTI3601 [SEQ ID NO:1]; GTI3602 [SEQ ID NO:2]; GTI3603 [SEQ ID NO:3]; GTI3604 [SEQ ID NO:4]; GTI3610 [SEQ ID NO:10]; GTI3611 [SEQ ID NO:11]; and GTI3612 [SEQ ID NO:12].
Figure 2B:
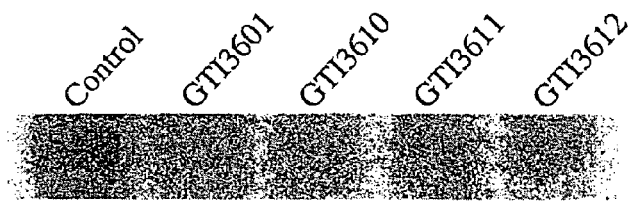

FIGS. 2A and 2B show that the antisense oligonucleotides reduce the neuropilin mRNA levels to at least 50% of the control cells.

Example 3

Inhibition of Human Tumor Cell Growth in Mice by Intravenous Treatment with Antisense Oligonucleotides Complementary to Neuropilin CD-1 athymic nude mice were purchased from Charles River Laboratories (Montreal Canada). HT-29 human colon cancer cells (typically $3 \times 10^6$ cells in 100 μl of PBS) were subcutaneously injected into the right flank of 6–7 weeks old CD-1 athymic female nude mice. Each experimental group included 5 mice. After the size of tumor reached an approximate volume of 100 mm$^3$, typically 5 days post tumor cell injection, the antisense oligonucleotide GTI3602 [SEQ ID NO:2] was administered by bolus infusion into the tail vein every other day at 10 mg/kg. Control animals received saline alone for the same period. Treatments typically lasted 14 days thereafter.

Figure 3A:
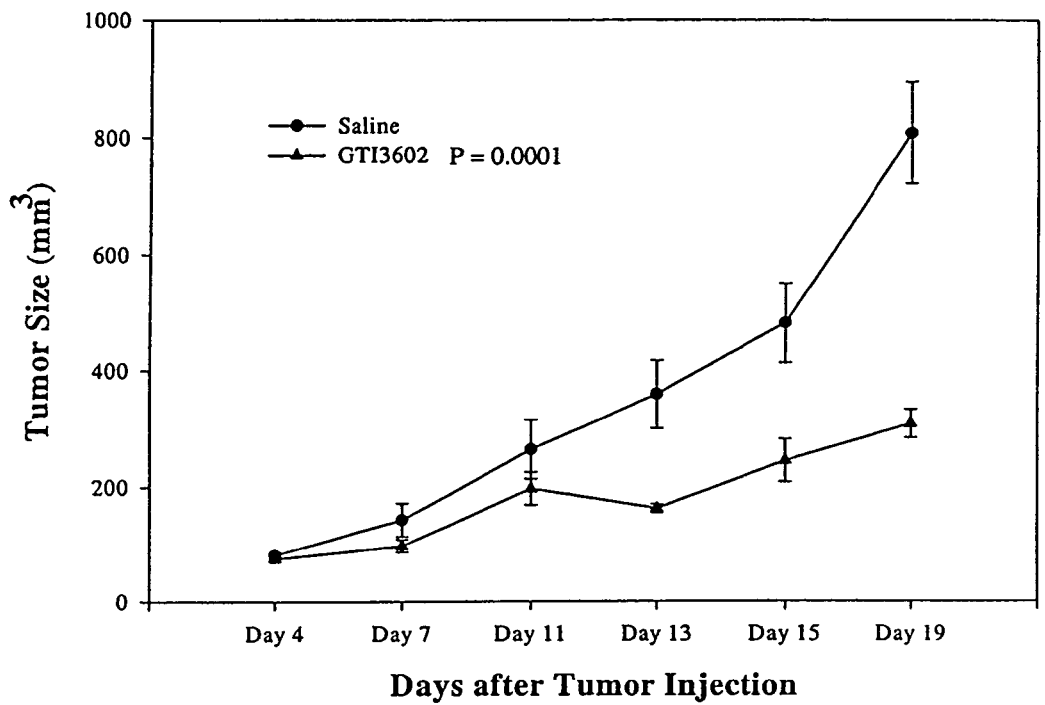
FIG. 3A is a graph of the volume of a tumor over time following injection of human HT-29 colon cancer cells into the right flank of mice with administration of antisense oligonucleotide GTI3602 [SEQ ID NO:2] or without (saline).

FIG. 3A shows the effects of the antisense oligonucleotide GTI3602 on HT-29 tumor growth in CD-1 nude mice. Antitumor activities were estimated by the inhibition of tumor volume, which was measured with a caliper on average of two day intervals over the span of 14 days. Each point in the figure represents mean tumor volume calculated from 5 animals per experimental group. Analysis of covariance was used to compare the regression curves of mice over time within each treatment group. Specific hypothesis of equality of slopes, or equality of intercepts when slopes are equal are derived from the analysis. All analysis used the SAS (Statistical Analysis System) version 6.12. When compared to the saline control, administration of the antisense oligonucleotide inhibited the growth of the tumor with a p value of $\leq 0.0001$.

Figure 3B:
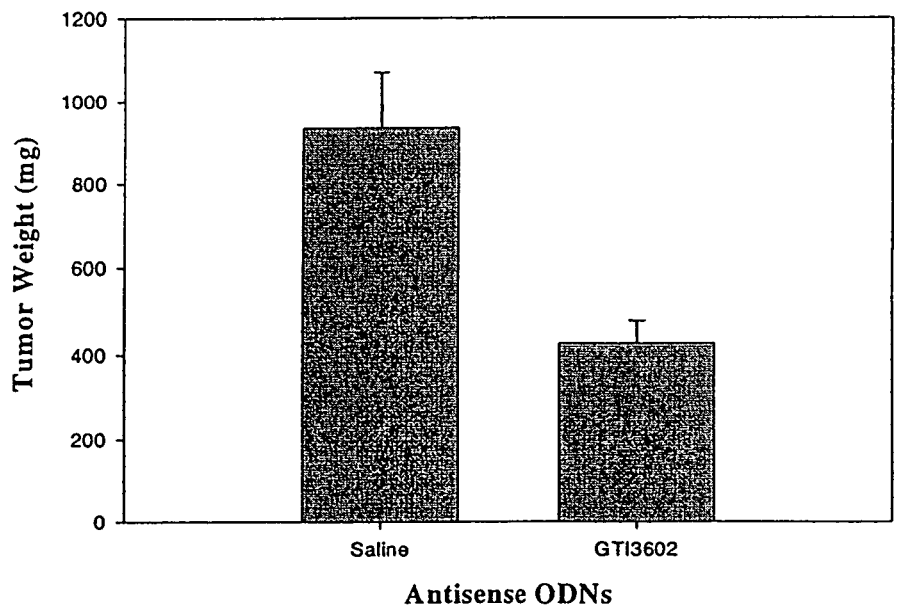
FIG. 3B is a graph of the weight of a tumor 20 days after injection of human HT-29 colon cancer cells into the right flank of mice with administration of antisense oligonucleotide GTI3602 [SEQ ID NO:2] or without (saline).

At the end of the treatment (usually 24 hours after the last treatment) the animals were sacrificed and tumor weights were measured. FIG. 3B shows the mean weight of the tumors. The antisense oligonucleotide showed significant inhibitory effects on tumor growth. One-way analysis of variance was used to compare the means of groups of treatments. Where the overall group effect was significant, a priori multiple comparisons using the least square means was used to find the pairs of treatment groups that were significantly different. When tumor weight was compared the antisense oligonucleotide also showed statistically significant inhibition when compared to the saline control.

Example 4

Inhibition of Experimental Metastasis by Antisense Oligonucleotides

Experimental metastasis of C8161 human melanoma cells treated with different antisense oligonucleotides was estimated as previously described (Fan et al., 1996[19]). Aliquots of cell suspension were seeded into 100 mm tissue culture dishes at a density of $2 \times 10^5$ and incubated overnight at 37° C. in α-MEM medium supplemented with 10% FBS. Cells were washed once in 10 ml of PBS and treated with 0.2 μM of oligonucleotides in the presence of cationic lipid (Lipofectin reagent, final concentration, 5 μg/ml, Gibco-BRL) for 4 hours. The antisense oligonucleotides were removed by washing the cells once with PBS and the cells were trypsinized. Cells were then collected by centrifugation, and approximately $1 \times 10^5$ cells suspended in 0.1 ml of PBS were injected into the tail veins of 6–8 week old CD-1 athymic female nude mice. Estimates of the number of lung tumors were made 5 weeks later, after excised lungs from individual mice were stained with picric acid dye solution (75% picric acid, 20% formaldehyde, 5% glacial acetic acid).

Figure 4:
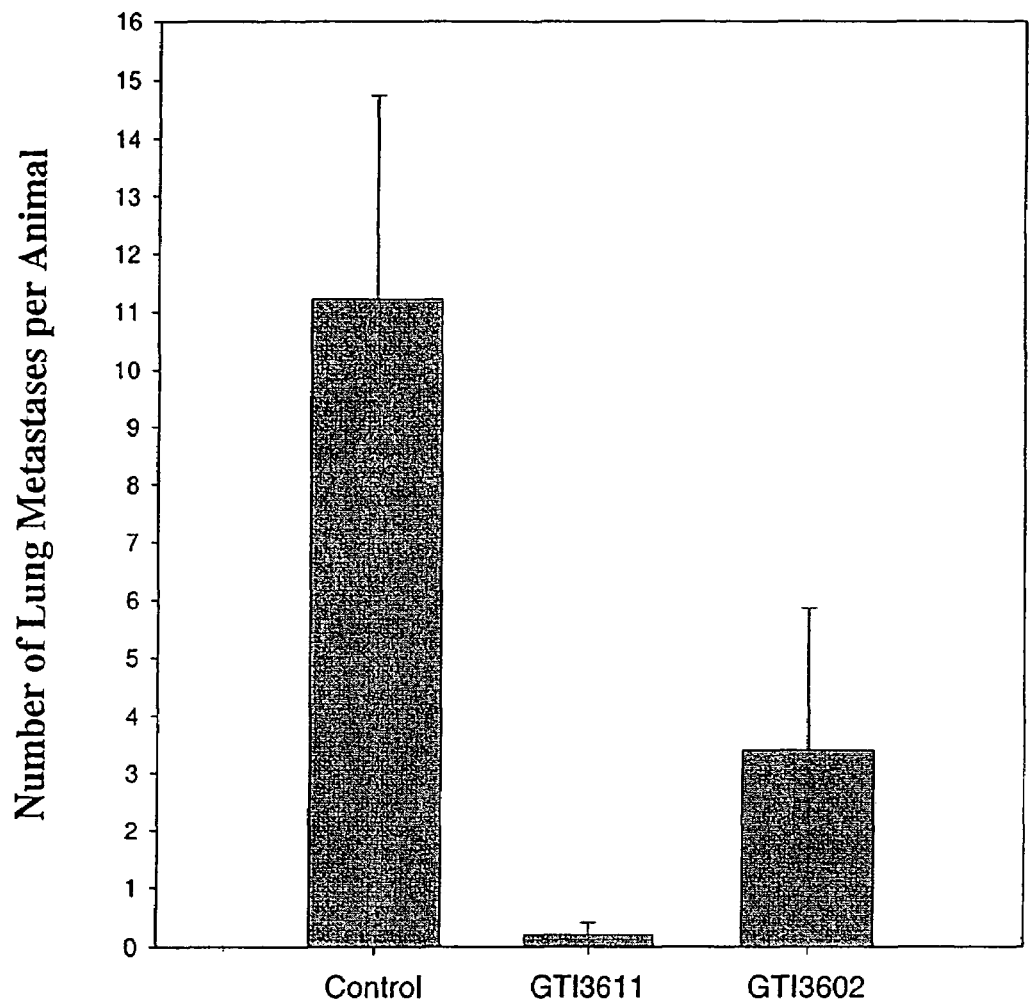
FIG. 4 is a graph of the average number of lung metastases per mouse by the human melanoma cell line C8161 after treatment of the cell line with the antisense oligonucleotides GTI3611 [SEQ ID NO:11] or GTI3602 [SEQ ID NO:2] or without [control].

FIG. 4 shows the reduced number of lung tumors in the female nude mice after treatment of the tumor cells with various antisense oligonucleotides.

The invention claimed is:

1. An antisense oligonucleotide from about 20 to 100 nucleotides in length comprising a sequence complementary to a human neuropilin mRNA, wherein said mRNA has a sequence as set forth in SEQ ID NO:33 and said antisense oligonucleotide comprises a sequence selected from the group consisting of SEQ ID NOs:1, 2, 3, 5, 6, 8, 9, 10, 11 and 12, and wherein said antisense oligonucleotide specifically binds to the nucleic acid comprising the sequence of said mRNA and inhibits neuropilin expression in the human and inhibits tumor cell growth in a human.

2. A vector comprising a sequence encoding an antisense oligonucleotide from about 20 to 100 nucleotides in length, said antisense oligonucleotide comprising a sequence complementary to a human neuropilin mRNA, wherein said mRNA has a sequence as set forth in SEQ ID NO:33 and said antisense oligonucleotide comprises a sequence selected from the group consisting of SEQ ID NOs:1, 2, 3, 5, 6, 8, 9, 10, 11 and 12, and wherein said antisense oligonucleotide specifically binds to the nucleic acid comprising the sequence of said mRNA and inhibits neuropilin expression in the human and inhibits tumor cell growth in the human.

3. A pharmaceutical composition comprising a pharmaceutically acceptable excipient and an effective amount of an antisense oligonucleotide from about 20 to 100 nucleotides in length comprising a sequence complementary to a human neuropilin mRNA, wherein said mRNA has a sequence as set forth in SEQ ID NO:33 and said antisense oligonucleotide comprises a sequence selected from the group consisting of SEQ ID NOs:1, 2, 3, 5, 6, 8, 9, 10, 11 and 12, and wherein said antisense oligonucleotide specifically binds to a nucleic acid comprising the sequence of said mRNA and inhibits neuropilin expression in a human and inhibits tumor cell growth in a human.

4. A method for inhibiting the growth of a human tumor comprising, administering to a human having the tumor an effective amount of an antisense oligonucleotide from about 20 to 50 nucleotides in length complementary to a human neuropilin mRNA under conditions such that the antisense oligonucleotide inhibits the growth of the tumor, wherein said mRNA has a sequence as set forth in SEQ ID NO:33, said tumor is derived from a carcinoma, and said antisense oligonucleotide specifically binds to a nucleic acid comprising the sequence of said mRNA.

5. The method according to claim 4 further comprising the step of administering to the human a chemotherapeutic agent.

6. The method according to claim 4 wherein the antisense oligonucleotide is from 20 to 50 nucleotides in length and comprises a sequence selected from the group consisting of SEQ ID NOs:1, 2, 3, 5, 6, 8, 9, 10, 11 and 12.

7. The method according to claim 4 wherein the antisense oligonucleotide is nuclease resistant.

8. A method of inhibiting the growth of human cancer cells comprising, contacting said cancer cells in vitro with an effective amount of an antisense oligonucleotide from about 20 to 50 nucleotides in length complementary to a human neuropilin mRNA, wherein said mRNA has a sequence as set forth in SEQ ID NO:33, under conditions such that the antisense oligonucleotide inhibits the growth of the cancer cells.

9. The method according to claim 8, wherein the antisense oligonucleotide is from 20 to 50 nucleotides in length and comprises a sequence selected from the group consisting of SEQ ID NOs:1, 2, 3, 5, 6, 8, 9, 10, 11 and 12.

10. The method according to claim 8 wherein the antisense oligonucleotide is nuclease resistant.

11. The method according to claim 4, comprising administering said antisense oligonucleotide by infusion.

12. The antisense oligonucleotide according to claim 1, wherein said antisense oligonucleotide consists of a sequence selected from the group consisting of SEQ ID NOs:1, 2, 3, 5, 6, 8, 9, 10, 11 and 12.

13. The antisense oligonucleotide according to claim 1, wherein said antisense oligonucleotide is a peptide nucleic acid.

14. The antisense oligonucleotide according to claim 1, wherein said antisense oligonucleotide comprises a morpholino backbone structure.

15. The antisense oligonucleotide according to claim 1, wherein said antisense oligonucleotide comprises at least one modified base selected from the group consisting of xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine, 8-halo guanines, 8-amino guanine, 8-thiol guanine, 8-thioalkyl guanines, 8-hydroxyl guanine, 5-trifluoromethyl uracil and 5-trifluoro cytosine.

16. The antisense oligonucleotide according to claim 1, wherein said antisense oligonucleotide comprises one or more modified internucleotide linkages in the phosphate backbone selected from the group consisting of methyl phosphonate, phosphorothioate, phosphorodithioate and phosphotriester internucleotide linkages.

17. The antisense oligonucleotide according to claim 1, wherein the antisense oligonucleotide comprises one or more phosphorothioate internucleotide linkages.

18. The antisense oligonucleotide according to claim 1, wherein the antisense oligonucleotide comprises one or more alkyl, cycloalkyl or heterocyclic intersugar linkages.

19. The antisense oligonucleotide according to claim 1, wherein the antisense oligonucleotide comprises at least one nucleotide that is a 2'-O-substituted ribonucleotide.

20. The antisense oligonucleotide according to claim 1, wherein said antisense oligonucleotide is nuclease resistant.

21. The vector according to claim 2, wherein said antisense oligonucleotide consists of a sequence selected from the group consisting of SEQ ID NOs:1, 2, 3, 5, 6, 8, 9, 10, 11 and 12.

22. The pharmaceutical composition according to claim 3 wherein said antisense oligonucleotide consists of a sequence selected from the group consisting of SEQ ID NOs:1, 2, 3, 5, 6, 8, 9, 10, 11 and 12.

23. The method according to claim 4, wherein said tumor is a cancer selected from the group consisting of melanoma, colon cancer, lung cancer, prostate cancer, pancreatic cancer and breast cancer.

24. A method of inhibiting colon cancer growth comprising, administering to a human having a colon cancer an effective amount of an antisense oligonucleotide from about 20 to 50 nucleotides in length complementary to a human neuropilin mRNA, wherein said mRNA has a sequence as set forth in SEQ ID NO:33, and wherein said antisense oligonucleotide inhibits the growth of the colon cancer in the human.

25. The method according to claim 24 further comprising the step of administering to the human a chemotherapeutic agent.

26. The method according to claim 24, wherein the antisense oligonucleotide is nuclease resistant.

27. The method according to claim 24, wherein the antisense oligonucleotide is from 20 to 50 nucleotides in length and comprises a sequence selected from the group consisting of SEQ ID NOs:1, 2, 3, 5, 6, 8, 9, 10, 11 and 12.

28. The method according to claim 24, wherein the antisense oligonucleotide consists of a sequence selected from the group consisting of SEQ ID NOs:1, 2, 3, 5, 6, 8, 9, 10, 11 and 12.

29. A method of inhibiting metastasis of a melanoma comprising, administering to a human having a melanoma an effective amount of an antisense oligonucleotide from about 20 nucleotides to 50 nucleotides in length complementary to a human neuropilin mRNA, wherein said mRNA has a sequence as set forth in SEQ ID NO:33, and wherein said oligonucleotide inhibits the metastasis of the melanoma in the human.

30. The method according to claim 29, further comprising the step of administering to the human a chemotherapeutic agent.

31. The method according to claim 29, wherein the oligonucleotide is nuclease resistant.

32. The method according to claim 29, wherein the oligonucleotide is from 20 to 50 nucleotides in length and comprises a sequence selected from the group consisting of SEQ ID NOs:1, 2, 3, 5, 6, 8, 9, 10, 11 and 12.

33. The method according to claim 29, wherein the oligonucleotide consists of a sequence selected from the group consisting of SEQ ID NOs:1, 2, 3, 5, 6, 8, 9, 10, 11 and 12.

34. The method according to claim 24, comprising administering said antisense oligonucleotide by infusion.

35. The method according to claim 29, comprising administering said antisense oligonucleotide by infusion.

36. The method according to claim 4, wherein the antisense oligonucleotide consists of a sequence selected from the group consisting of SEQ ID NOs:1, 2, 3, 5, 6, 8, 9, 10, 11 and 12.

37. The method according to claim 8, wherein the antisense oligonucleotide consists of a sequence selected from the group consisting of SEQ ID NOs:1, 2, 3, 5, 6, 8, 9, 10, 11 and 12.

38. The antisense oligonucleotide according to claim 1, wherein the antisense oligonucleotide is from about 20 to 50 nucleotides in length.

39. The vector according to claim 2, wherein the antisense oligonucleotide is from about 20 to 50 nucleotides in length.

40. The pharmaceutical composition according to claim 3, wherein the antisense oligonucleotide is from about 20 to 50 nucleotides in length.

* * * * *